United States Patent
Chackalamannil et al.

(10) Patent No.: US 7,304,078 B2
(45) Date of Patent: Dec. 4, 2007

(54) THROMBIN RECEPTOR ANTAGONISTS

(75) Inventors: Samuel Chackalamannil, Califon, NJ (US); William J. Greenlee, Teaneck, NJ (US); Yuguang Wang, North Brunswick, NJ (US); Wenxue Wu, Princeton Junction, NJ (US); Enrico P. Veltri, Princeton, NJ (US); Yan Xia, Edison, NJ (US)

(73) Assignee: Schering Corporation, Kenilworth, NJ (US)

( * ) Notice: Subject to any disclaimer, the term of this patent is extended or adjusted under 35 U.S.C. 154(b) by 358 days.

(21) Appl. No.: 10/412,982

(22) Filed: Apr. 14, 2003

(65) Prior Publication Data

US 2003/0216437 A1 Nov. 20, 2003

Related U.S. Application Data

(60) Provisional application No. 60/373,072, filed on Apr. 16, 2002.

(51) Int. Cl.
*A61K 31/443* (2006.01)
*C07D 405/02* (2006.01)

(52) U.S. Cl. .................... 514/337; 546/284.1; 514/337
(58) Field of Classification Search .............. 546/284.1; 514/337
See application file for complete search history.

(56) References Cited

U.S. PATENT DOCUMENTS

| | | | |
|---|---|---|---|
| 4,847,265 A | 7/1989 | Badorc et al. | |
| 5,576,328 A | 11/1996 | Herbert et al. | |
| 6,063,847 A * | 5/2000 | Chackalamannil et al. . | 524/297 |
| 6,326,380 B1 | 12/2001 | Chackalamannil .......... | 514/311 |
| 6,429,210 B1 | 8/2002 | Bousquet et al. | |
| 6,504,030 B1 | 1/2003 | Bousquet et al. | |
| 6,645,987 B2 | 11/2003 | Chackalamannil et al. | |
| 6,894,065 B2 | 5/2005 | Chackalamannil et al. | |
| 7,037,920 B2 | 5/2006 | Chackalamannil et al. | |
| 2003/0203927 A1 | 10/2003 | Chackalamannil .......... | 514/291 |
| 2004/0152736 A1 | 8/2004 | Chackalamannil et al. | |
| 2004/0192753 A1 | 9/2004 | Chackalamannil et al. | |
| 2006/0106050 A1 | 5/2006 | Chakalamannil et al. | |

FOREIGN PATENT DOCUMENTS

| WO | WO 99/26943 | 6/1999 |
|---|---|---|
| WO | WO99/26943 | * 6/1999 |
| WO | WO 01/96330 | 12/2001 |

OTHER PUBLICATIONS

International Search Report; mailed Jul. 22, 2003, PCT #US 03/11510.
U.S. Appl. No. 10/755,066, filed Jul. 9, 2005.
Hsieh, et. al.; "Simultaneous determination of a drug candidate and its metabolite in rate plasma samples using ultrafast monolithic column high-performance liquid chromatography/tandem mass spectrometry"; Rapid Communications in Mass Spectrometry; 2002;16:944-950.
Bernatowicz; "Development of Potent Thrombin Receptor Antagonist Peptides"; J. Med. Chem.; 1996; 39:4879-4887.
Ahn, Ho-Sam et al. Binding of a thrombin receptor tethered ligand analogue to human platelet thrombin receptor. Mol Pharmacol. Feb. 1997;51(2):350-6.
Zhang, Han-Cheng et al. Discovery and optimization of a novel series of thrombin receptor (par-1) antagonists: potent, selective peptide mimetics based on indole and indazole templates. J Med Chem. Mar. 29, 2001;44(7):1021-4.
Zhang, H.-C. et al; "Discovery and Optimization of a Novel Series of Thrombin Receptor (PAR-1) Antagonists: Potent, Selective Peptide Mimetics Based on Indole and Indazole Templates" J. Med. Chem.; (Letter); 2001; 44(7); 1021-1024.
Shaun R. Coughlin; "How the protease thrombin talks to cells."; Proc. Natl. Acad. Sci. USA, vol. 98, pp. 11023-11027, Sep. 1999.

(Continued)

*Primary Examiner*—Joseph K. McKane
*Assistant Examiner*—Janet L. Coppins
(74) *Attorney, Agent, or Firm*—Gerald E. Reinhardt

(57) ABSTRACT

Heterocyclic-substituted tricyclics of the formula

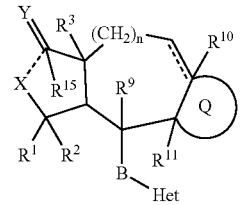

or a pharmaceutically acceptable salt thereof, wherein:
the dotted line represents an optional single bond;
-----represents an optional double bond;
n is 0–2;
Q is cycloalkyl, optionally substituted by $R^{13}$ and $R^{14}$;
$R^{13}$ and $R^{14}$ are independently selected from $(C_1-C_6)$ alkyl, $(C_3-C_8)$cycloalkyl, —OH, $(C_1-C_6)$alkoxy, $R^{27}$-aryl$(C_1-C_6)$alkyl, heteroaryl, heteroarylalkyl, heterocyclyl, heterocyclylalkyl, halogen and haloalkyl; or
$R^{13}$ and $R^{14}$ together form a spirocyclic or a heterospirocyclic ring of 3–6 atoms;
Het is a mono- or bi-cyclic optionally substituted heteroaryl group; and
B is a bond, alkylene, or optionally substituted alkenylene or alkynylene, wherein the remaining substituents are as defined in the specification, are disclosed, as well as pharmaceutical compositions containing them and a method of treating diseases associated with thrombosis, atherosclerosis, restenosis, hypertension, angina pectoris, arrhythmia, heart failure, and cancer by administering said compounds. Combination therapy with other cardiovascular agents is also claimed.

67 Claims, No Drawings

OTHER PUBLICATIONS

Grand Roger J.A. et al; "Cellular consequences of thrombin-receptor activation", Biochem. J. 1996, vol. 313, pp. 353-368 (printed in Great Britain).

Ahn H S et al; "Nonpeptide thrombin receptor antagonists,". Drugs of the Future 2001, 26 (11); 1065-1085.

Samuel Chackalamannil; "Thrombin receptor antagonists as novel therapeutic targets", Drug Discovery & Development 2001. vol. 4, No. 4, pp. 417-427 @ PharmaPress Ltd ISN 1387-6733.

Office Action issued on Jan. 20, 2006 in the corresponding application before the European Patent Office (03 718 393.6-2117).

Response thereto submitted on Jul. 28, 2006 in the corresponding application before the European Patent Office (03 718 393.6-2117).

Fig. 1
Fig. 2
Fig. 3
Fig. 4
Fig. 5
Fig. 6
Fig. 7
Fig. 8
Fig. 9
Fig. 10
Fig. 11
Fig. 12
Fig. 13
Fig. 14

* cited by examiner

THROMBIN RECEPTOR ANTAGONISTS

The present application claims priority under 35 USC section 119(e) of U.S. Provisional application Ser. No. 60/373,072, filed Apr. 16, 2002, the complete text, claims and figures of which are incorporated by reference herein as if fully set forth.

BACKGROUND OF THE INVENTION

The present invention relates to substituted tricyclic thrombin receptor antagonists, pharmaceutical compositions containing them and their use in the treatment of diseases associated with thrombosis, atherosclerosis, restenosis, hypertension, angina pectoris, arrhythmia, heart failure, cerebral ischemia, stroke, inflammatory disorders, neurodegenerative diseases and cancer. The invention also relates to the combination of novel compounds of the invention and other cardiovascular agents.

Thrombin is known to have a variety of activities in different cell types and thrombin receptors are known to be present in such cell types as human platelets, vascular smooth muscle cells, endothelial cells and fibroblasts. It is therefore possible that thrombin receptor antagonists, also known as protease activated receptor (PAR) antagonists will be useful in the treatment of thrombotic, inflammatory, atherosclerotic and fibroproliferative disorders, as well as other disorders in which thrombin and its receptor play a pathological role.

Thrombin receptor antagonists peptides have been identified based on structure-activity studies involving substitutions of amino acids on thrombin receptors. In Bernatowicz et al, *J. Med. Chem.*, vol. 39, pp. 4879–4887 (1996), tetra- and pentapeptides are disclosed as being potent thrombin receptor antagonists, for example N-trans-cinnamoyl-p-fluoroPhe-p-guanidinoPhe-Leu-Arg-NH$_2$ and N-trans-cinnamoyl-p-fluoroPhe-p-guanidinoPhe-Leu-Arg-Arg-NH$_2$. Peptide thrombin receptor antagonists are also disclosed in WO 94/03479, published Feb. 17, 1994.

Substituted tricyclic thrombin receptor antagonists are disclosed in U.S. Pat. Nos. 6,063,847, 6,326,380 and U.S. Ser. No. 09/880,222 (WO 01/96330) and 10/271,715.

SUMMARY OF THE INVENTION

The present invention relates to thrombin receptor antagonists represented by the Formula I:

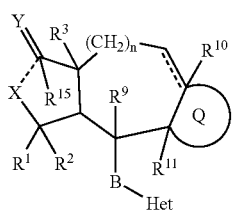

or a pharmaceutically acceptable salt or solvate thereof, wherein:

the single dotted line represents an optional single bond;

-----represents an optional double bond;

n is 0–2;

Q is

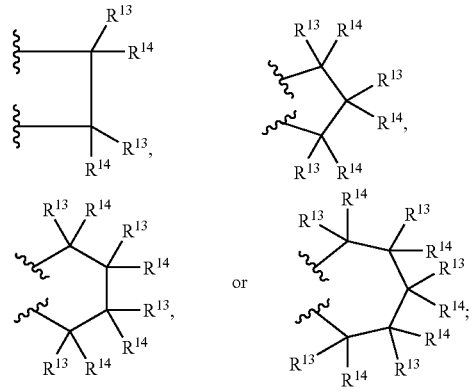

$R^1$ is independently selected from the group consisting of H, $(C_1-C_6)$alkyl, fluoro$(C_1-C_6)$alkyl-, difluoro$(C_1-C_6)$alkyl-, trifluoro-$(C_1-C_6)$alkyl-, $(C_3-C_6)$cycloalkyl, $(C_2-C_6)$alkenyl, hydroxy-$(C_1-C_6)$alkyl-, and amino$(C_1-C_6)$alkyl-;

$R^2$ is independently selected from the group consisting of H, $(C_1-C_6)$alkyl, fluoro$(C_1-C_6)$alkyl-, difluoro$(C_1-C_6)$alkyl-, trifluoro-$(C_1-C_6)$alkyl-, $(C_3-C_6)$cycloalkyl, $(C_2-C_6)$alkenyl, hydroxy-$(C_1-C_6)$alkyl-, and amino$(C_1-C_6)$alkyl-;

$R^3$ is H, hydroxy, $(C_1-C_6)$alkoxy, —SOR$^{16}$, —SO$_2$R$^{17}$, —C(O)OR$^{17}$, —C(O)NR$^{18}$R$^{19}$, —$(C_1-C_6)$alkyl-C(O)NR$^{18}$R$^{19}$, $(C_1-C_6)$alkyl, halogen, fluoro$(C_1-C_6)$alkyl-, difluoro$(C_1-C_6)$alkyl-, trifluoro$(C_1-C_6)$alkyl-, $(C_3-C_6)$cycloalkyl, $(C_3-C_6)$-cycloalkyl-$(C_1-C_6)$alkyl-, $(C_2-C_6)$alkenyl, aryl$(C_1-C_6)$alkyl-, aryl$(C_2-C_6)$alkenyl-, heteroaryl $(C_1-C_6)$alkyl-, heteroaryl$(C_2-C_6)$alkenyl-, hydroxy $(C_1-C_6)$-alkyl-, —NR$^{22}$R$^{23}$, NR$^{22}$R$^{23}$—$(C_1-C_6)$alkyl-, aryl, thio$(C_1-C_6)$alkyl-, $(C_1-C_6)$alkyl-thio$(C_1-C_6)$alkyl-, $(C_1-C_6)$alkoxy$(C_1-C_6)$alkyl-, NR$^{18}$R$^{19}$—C(O)—$(C_1-C_6)$alkyl- or $(C_3-C_6)$cycloalkyl-$(C_1-C_6)$alkyl-;

Het is a mono- or bi-cyclic heteroaryl group of 5 to 10 atoms comprised of 1 to 9 carbon atoms and 1 to 4 heteroatoms independently selected from the group consisting of N, O and S, wherein a ring nitrogen can form an N-oxide or a quaternary group with a $C_1-C_4$ alkyl group, wherein Het is attached to B by a carbon atom ring member, and wherein the Het group is substituted by W;

W is 1 to 4 substituents independently selected from the group consisting of H, $(C_1-C_6)$alkyl, fluoro$(C_1-C_6)$alkyl-, difluoro$(C_1-C_6)$alkyl-, trifluoro$(C_1-C_6)$alkyl-, $(C_3-C_6)$cycloalkyl, hydroxy$(C_1-C_6)$alkyl-, dihydroxy$(C_1-C_6)$alkyl-, NR$^{25}$R$^{26}$$(C_1-C_6)$alkyl-, thio$(C_1-C_6)$alkyl-, —OH, $(C_1-C_6)$alkoxy, halogen, —NR$^4$R$^5$, —C(O)OR$^{17}$, —C(O)R$^{16}$, $(C_1-C_6)$alkylthio-, R$^{21}$-aryl, R$^{21}$-aryl$(C_1-C_6)$alkyl-, aryl wherein adjacent carbons form a ring comprising a methylenedioxy group, and R$^{21}$-heteroaryl;

$R^4$ and $R^5$ are independently selected from the group consisting of H, $(C_1-C_6)$alkyl, phenyl, benzyl and $(C_3-C_6)$cycloalkyl, or $R^4$ and $R^5$ taken together are —(CH$_2$)$_4$—, —(CH$_2$)$_5$— or —(CH$_2$)$_2$NR$^7$—(CH$_2$)$_2$— and form a ring with the nitrogen to which they are attached;

$R^6$ is H, $(C_1-C_6)$alkyl or phenyl;

$R^7$ is H, $(C_1-C_6)$alkyl, —C(O)—R$^{16}$, —C(O)OR$^{17}$ or —SO$_2$R$^{17}$;

$R^8$, $R^{10}$ and $R^{11}$ are independently selected from the group consisting of $R^1$ and —OR$^1$, provided that when the optional double bond is present, $R^{10}$ is absent;

$R^9$ is H, OH or $(C_1–C_6)$alkoxy;

B is —$(CH_2)_{n3}$—, cis or trans —$(CH_2)_{n4}CR^{12}$=$CR^{12a}(CH_2)_{n5}$ or —$(CH_2)_{n4}C$≡$C(CH_2)_{n5}$—, wherein $n_3$ is 0–5, $n_4$ and $n_5$ are independently 0–2, and $R^{12}$ and $R^{12a}$ are independently selected from the group consisting of H, $(C_1–C_6)$ alkyl and halogen;

X is —O— or —$NR^6$— when the dotted line represents a single bond, or X is —OH or —$NHR^{20}$ when the bond is absent;

Y is =O, =S, (H, H), (H, OH) or (H, $(C_1–C_6)$alkoxy) when the dotted line represents a single bond, or when the bond is absent, Y is =O, (H, H), (H, OH), (H, SH) or (H, $(C_1–C_6)$alkoxy);

each $R^{13}$ is independently selected from H, $(C_1–C_6)$alkyl, $(C_3–C_8)$cycloalkyl, —$(CH_2)_{n6}NHC(O)OR^{16b}$, —$(CH_2)_{n6}NHC(O)R^{16b}$, —$(CH_2)_{n6}NHC(O)NR^4R^5$, —$(CH_2)_{n6}NHSO_2R^{16}$, —$(CH_2)_{n6}NHSO_2NR^4R^5$, and —$(CH^2)_{n6}C(O)NR^{28}R^{29}$ where $n_6$ is 0–4, haloalkyl, and halogen;

each $R^{14}$ is independently selected from H, $(C_1–C_6)$alkyl, —OH, $(C_1–C_6)$alkoxy, $R^{27}$-aryl$(C_1–C_6)$alkyl, heteroaryl, heteroarylalkyl, heterocyclyl, heterocyclylalkyl, —$(CH_2)_{n6}NHC(O)OR^{16b}$, —$(CH_2)_{n6}NHC(O)R^{16b}$, —$(CH_2)_{n6}NHC(O)NR^4R^5$, —$(CH_2)_{n6}NHSO_2R^{16}$, —$(CH_2)_{n6}NHSO_2NR^4R^5$, and —$(CH_2)_{n6}C(O)NR^{28}R^{29}$ where $n_6$ is 0–4, halogen and haloalkyl; or $R^{13}$ and $R^{14}$ taken together form a spirocyclic or a heterospirocyclic ring of 3–6 atoms;

wherein at least one of $R^{13}$ or $R^{14}$ is selected from the group consisting of —$(CH_2)_{n6}NHC(O)OR^{16b}$, —$(CH_2)_{n6}NHC(O)R^{16b}$, —$(CH_2)_{n6}NHC(O)NR^4R^5$, —$(CH_2)_{n6}NHSO_2R^{16}$, —$(CH_2)_{n6}NHSO_2NR^4R^5$, and —$(CH^2)_{n6}C(O)NR^{28}R^{29}$ where $n_6$ is 0–4;

$R^{15}$ is absent when the dotted line represents a single bond and is H, $(C_1–C_6)$alkyl, —$NR^{18}R^{19}$, or —$OR^{17}$ when the bond is absent;

$R^{16}$ is independently selected from the group consisting of $(C_1–C_6)$alkyl, phenyl and benzyl;

$R^{16b}$ is H, alkoxy, $(C_1–C_6)$alkyl, $(C_1–C_6)$alkoxy$(C_1–C_6)$alkyl-, $R^{22}$—O—C(O)—$(C_1–C_6)$alkyl-, $(C_3–C_6)$cycloalkyl, $R^{21}$-aryl, $R^{21}$-aryl$(C_1–C_6)$alkyl, haloalkyl, alkenyl, halosubstituted alkenyl, alkynyl, halosubstituted alkynyl, $R^{21}$-heteroaryl, $R^{21}$—$(C_1–C_6)$alkyl heteroaryl, $R^{21}$—$(C_1–C_6)$alkyl heterocycloalkyl, $R^{28}R^{29}$N—$(C_1–C_6)$alkyl, $R^{28}R^{29}$N—(CO)—$(C_1–C_6)$alkyl, $R^{28}R^{29}$N—(CO)O—$(C_1–C_6)$alkyl, $R^{28}$O(CO)N$(R^{29})$—$(C_1–C_6)$alkyl, $R^{28}$S(O)$_2$N$(R^{29})$—$(C_1–C_6)$alkyl, $R^{28}R^{29}$N—(CO)—N$(R^{29})$—$(C_1–C_6)$alkyl, $R^{28}R^{29}$N—S(O)2N$(R^{29})$—$(C_1–C_6)$alkyl, $R^{28}$—(CO)N$(R^{29})$—$(C_1–C_6)$alkyl, $R^{28}R^{29}$N—S(O)$_2$—$(C_1–C_6)$alkyl, HOS(O)$_2$—$(C_1–C_6)$alkyl, (OH)$_2$P(O)$_2$—$(C_1–C_6)$alkyl, $R^{28}$—S—$(C_1–C_6)$alkyl, $R^{28}$—S(O)$_2$—$(C_1–C_6)$alkyl or hydroxy$(C_1–C_6)$alkyl);

$R^{17}$, $R^{18}$ and $R^{19}$ are independently selected from the group consisting of H, $(C_1–C_6)$alkyl, phenyl, and benzyl;

$R^{20}$ is H, $(C_1–C_6)$alkyl, phenyl, benzyl, —C(O)$R^6$ or —SO$_2R^6$;

$R^{21}$ is 1 to 3 substituents independently selected from the group consisting of H, —CN, —CF$_3$, —OCF$_3$, halogen, —NO$_2$, $(C_1–C_6)$alkyl, —OH, $(C_1–C_6)$alkoxy, $(C_1–C_6)$-alkylamino-, di-(($C_1–C_6$)alkyl)amino-, $NR^{25}R^{26}$-$(C_1–C_6)$alkyl-, hydroxy-$(C_1–C_6)$alkyl-, —C(O)$OR^{17}$, —$COR^{17}$, —NH$COR^{16}$, —NHSO$_2R^{16}$, —NHSO$_2$CH$_2$CF$_3$, —C(O)$NR^{25}R^{26}$, —$NR^{25}$—C(O)—$NR^{25}R^{26}$, —S(O)$R^{13}$, —S(O)$_2R^{13}$ and —S$R^{13}$;

$R^{22}$ is H or $(C_1–C_6)$alkyl;

$R^{23}$ is H, $(C_1–C_6)$alkyl, —C(O)$R^{24}$, —SO$_2R^{24}$, —CONHR$^{24}$ or —SO$_2$NHR$^{24}$;

$R^{24}$ is $(C_1–C_6)$alkyl, hydroxy $(C_1–C_6)$alkyl or $NR^{25}R^{26}$—(($C_1–C_6$)alkyl)-;

$R^{25}$ and $R^{26}$ are independently selected from the group consisting of H and $(C_1–C_6)$alkyl;

$R^{27}$ is 1, 2 or 3 substituents selected from the group consisting of H, $(C_1–C_6)$alkyl, $(C_3–C_6)$cycloalkyl, $(C_1–C_6)$ alkoxy, halogen and —OH; and $R^{28}$ and $R^{29}$ are independently selected from the group consisting of H, $(C_1–C_6)$alkyl, $(C_1–C_6)$alkoxy, $R^{27}$-aryl $(C_1–C_6)$alkyl, heteroaryl, heteroarylalkyl, hydroxy$(C_1–C_6)$ alkyl, $(C_1–C_6)$alkoxy$(C_1–C_6)$alkyl, heterocyclyl, heterocyclylalkyl, and haloalkyl; or $R^{28}$ and $R^{29}$ taken together form a spirocyclic or a heterospirocyclic ring of 3–6 atoms.

Thrombin receptor antagonist compounds of the present invention can have anti-thrombotic, anti-platelet aggregation, antiatherosclerotic, antirestenotic and/or anti-coagulant activity. Thrombosis-related diseases treated by the compounds of this invention include thrombosis, atherosclerosis, restenosis, hypertension, angina pectoris, arrhythmia, heart failure, myocardial infarction, glomerulonephritis, thrombotic and thromboembolytic stroke, peripheral vascular diseases, other cardiovascular diseases, cerebral ischemia, inflammatory disorders and cancer, as well as other disorders in which thrombin and its receptor play a pathological role.

Certain embodiments of this invention also relate to a method of using at least one compound of Formula I in combination with one or more additional cardiovasular agents for the treatment of thrombosis, platelet aggregation, coagulation, cancer, inflammatory diseases or respiratory diseases, comprising administering a combination of at least one compound of formula I and at least one additional cardiovascular agent to a mammal in need of such treatment. In particular, the present invention relates to a method of using said combination in the treatment of thrombosis, atherosclerosis, restenosis, hypertension, angina pectoris, arrhythmia, heart failure, myocardial infarction, glomerulonephritis, thrombotic stroke, thromboembolic stroke, peripheral vascular diseases, cerebral ischemia, cancer, rheumatoid arthritis, systemic lupus erythematosus, multiple sclerosis, diabetes, osteoporosis, renal ischemia, cerebral stroke, cerebral ischemia, nephritis, inflammatory disorders of the lungs and gastrointestinal tract, reversible airway obstruction, chronic asthma or bronchitis. It is contemplated that a combination of this invention may be useful in treating more than one of the diseases listed.

Some embodiments of the invention relate to a pharmaceutical composition comprising a therapeutically effective amount of a combination of at least one compound of formula I and at least one additional cardiovascular agent in a pharmaceutically acceptable carrier.

Some embodiments of the invention relate to the use of a thrombin receptor antagonist disclosed in any of U.S. Pat. Nos. 6,063,847, 6,326,380, U.S. Ser. Nos. 09/880,222 and 10/271,715, all of which are incorporated herein by reference, in combination with one or more additional cardiovascular agents, for the treatment of thrombosis, platelet aggregation, coagulation, cancer, inflammatory diseases or respiratory diseases. In particular, the present invention relates to a method of using said combination in the treatment of thrombosis, atherosclerosis, restenosis, hypertension, angina pectoris, arrhythmia, heart failure, myocardial infarction, glomerulonephritis, thrombotic stroke, thromboembolic stroke, peripheral vascular diseases, cerebral ischemia, cancer, rheumatoid arthritis, systemic lupus erythematosus, multiple sclerosis, diabetes, osteoporosis, renal ischemia, cerebral stroke, cerebral ischemia, nephritis, inflammatory disorders of the lungs and gastrointestinal tract, reversible airway obstruction, chronic asthma or bronchitis.

It is further contemplated that the combination of the invention can be provided as a kit comprising in a single package at least one compound of formula I in a pharmaceutical composition, and at least one separate pharmaceutical composition comprising a cardiovascular agent.

DETAILED DESCRIPTION

For compounds of Formula I, preferred definitions of the variables are as follows:

The variable n is preferably 0–2, and more preferably 0. The optional double bond is preferably absent (i.e., the bond is a single bond).

Q is preferably:

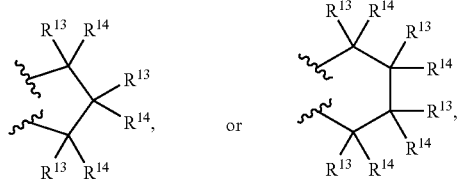

with the six-membered Q ring being more preferred. $R^{13}$ is preferably H or —$CH_3$. $R^{14}$ is preferably H or —$CH_3$. For the five-membered Q ring, preferably no more than two $R^{13}$ and $R^{14}$ substituents are other than hydrogen. For the six-membered Q ring, preferably no more than four $R^{13}$ and $R^{14}$ substituents are other than hydrogen, more preferably no more than two $R^{13}$ and $R^{14}$ substituents are other than hydrogen.

Especially preferred Q rings are:

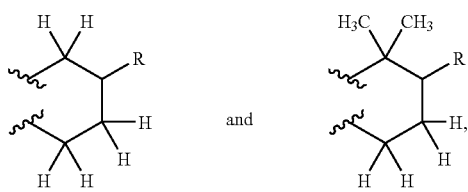

preferably shown as

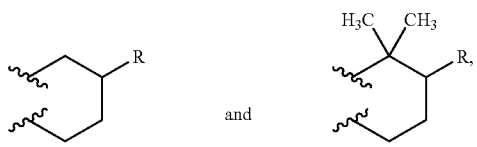

respectively.

In the preferred Q rings above, R is preferably —$(CH_2)_{n6}$NHC(O)OR$^{16b}$, —$(CH_2)_{n6}$NHC(O)R$^{16b}$, —$(CH_2)_{n6}$NHC(O)NR$^4$R$^5$, —$(CH_2)_{n6}$NHSO$_2$R$^{16}$ or —$(CH_2)_{n6}$NHSO$_2$NR$^4$R$^5$ wherein $n_6$ is 0–2, and R$^{16b}$, R$^{16}$ and R$^4$ are ($C_1$–$C_6$)alkyl and R$^5$ is H. More preferred are compounds of Formula I wherein R is —NHC(O)OR$^{16b}$, —NHC(O)R$^{16b}$, —NHC(O)NR$^4$R$^5$, —NHSO$_2$R$^{16}$ or —NHSO$_2$NR$^4$R$^5$ wherein R$^{16b}$, R$^{16}$ and R$^4$ are ($C_1$–$C_6$)alkyl and R$^5$ is H. Even more preferred are compounds of Formula I wherein R is —NHC(O)OR$^{16b}$, —NHC(O)R$^{16b}$ or —NHC(O)NR$^4$R$^5$, wherein R$^{16b}$ and R$^4$ are ($C_1$–$C_6$)alkyl and R$^5$ is H.

$R^1$ and $R^2$ are preferably independently selected from the group consisting of H and ($C_1$–$C_6$)alkyl; more preferably, $R^1$ is ($C_1$–$C_6$)alkyl and $R^2$ is H; especially preferred are compounds wherein $R^1$ is —$CH_3$ and $R^2$ is H.

$R^3$ is preferably H, —OH, ($C_1$–$C_6$)alkyl, ($C_1$–$C_6$)alkoxy, halogen, ($C_3$–$C_6$)cycloalkyl, —C(O)OR$^{17}$ or —NR$^{22}$R$^{23}$; more preferably, $R^3$ is H or ($C_1$–$C_6$)alkyl.

Het is preferably pyridyl attached to B by a carbon ring member, and is preferably substituted by 1 or 2 substituents selected from W, more preferably 1 substituent. W is preferably R$^{21}$-aryl or R$^{21}$-heteroaryl. Aryl is preferably phenyl. Heteroaryl is preferably pyridyl. $R^{21}$ is preferably H, halogen or —CN, or —$CF_3$, especially F, —CN or —$CF_3$.

$R^8$, $R^{10}$ and $R^{11}$ are each independently preferably H or ($C_1$–$C_6$)alkyl, more preferably H or —$CH_3$; especially preferred are compounds of Formula I wherein $R^8$, $R^{10}$ and $R^{11}$ are each H.

$R^9$ is preferably H, OH or ($C_1$–$C_6$)alkoxy; more preferably, $R^9$ is H.

B is preferably cis or trans —$(CH_2)_{n4}CR^{12}$=$CR^{12a}(CH_2)_{n5}$— wherein $n_4$, $n_5$, $R^{12}$ and $R^{12a}$ are as defined above; more preferably, $R^{12}$ and $R^{12a}$ are each H, and $n_4$ and $n_5$ are each zero. Particularly preferred are compounds wherein B is trans-alkenyl, especially —CH=CH—.

One group of preferred compounds is that wherein the optional single bond is present, X is —O—, Y is =O, and $R^{15}$ is absent. Another preferred group of compounds is that wherein the optional single bond is absent, X is —OH, Y is (H, OH) and $R^{15}$ is H. Compounds wherein the optional single bond is present, X is —O—, Y is =O, and $R^{15}$ is absent are more preferred.

Especially preferred are compounds of Formula I wherein R is —NHC(O)OR$^{16b}$ wherein R$^{16b}$ is ($C_1$–$C_6$)alkyl. R$^{16b}$ is preferably methyl or ethyl. Also preferred are compounds wherein the R group is attached to the C-7 position of the Q ring, as shown in Formula IA below.

A preferred embodiment of the invention is a compound of Formula IA:

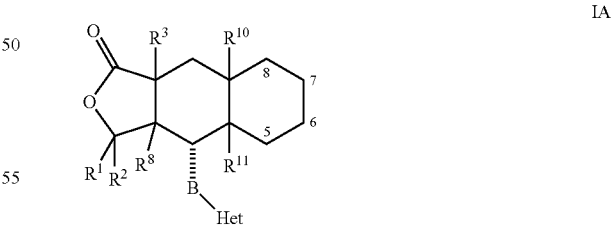

wherein $R^1$, $R^2$, $R^3$, $R^8$, $R^{10}$, $R^{11}$, B, and Het are defined as preferred above. At least one of ring carbon atoms 5–8 is preferably substituted with —$(CH_2)_{n6}$NHC(O)OR$^{16b}$, —$(CH_2)_{n6}$NHCOR$^{16b}$, —$(CH_2)_{n6}$NHCONR$^4$R$^5$, —$(CH_2)_{n6}$NHSO$_2$R$^{16}$ or —$(CH_2)_{n6}$NHSO$_2$NR$^4$R$^5$ wherein $n_6$ is 0–2, and R$^{16b}$, R$^{16}$ and R$^4$ are ($C_1$–$C_6$)alkyl and R$^5$ is H.

A more preferred embodiment of the invention is a compound of Formula IB:

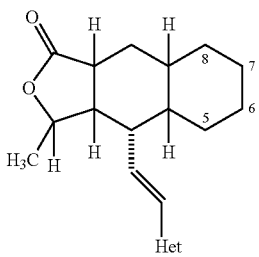

wherein Het is pyridyl substituted by an $R^{21}$-aryl group, preferably an $R^{21}$-phenyl group wherein $R^{21}$ is preferably F or —$CF_3$.

Especially preferred are compounds of Formula IA or 1 B wherein at least one of ring carbon atoms 5–8 is —NHC(O)O$R^{16b}$ wherein $R^{16b}$ is ($C_1$–$C_6$)alkyl. $R^{16b}$ is preferably methyl or ethyl.

As used above, and throughout the specification, the following terms, unless otherwise indicated, shall be understood to have the following meanings:

"Subject" includes both mammals and non-mammalian animals.

"Mammal" includes humans and other mammalian animals.

The term "optionally substituted" means optional substitution with the specified groups, radicals or moieties. It should be noted that any atom with unsatisfied valences in the text, schemes, examples and tables herein is assumed to have the hydrogen atom(s) to satisfy the valences.

The following definitions apply regardless of whether a term is used by itself or in combination with other terms, unless otherwise indicated. Therefore, the definition of "alkyl" applies to "alkyl" as well as the "alkyl" portions of "hydroxyalkyl", "haloalkyl", "alkoxy", etc.

As used herein, the term "alkyl" means an aliphatic hydrocarbon group that can be straight or branched and comprises 1 to about 20 carbon atoms in the chain. Preferred alkyl groups comprise 1 to about 12 carbon atoms in the chain. More preferred alkyl groups comprise 1 to about 6 carbon atoms in the chain. "Branched" means that one or more lower alkyl groups such as methyl, ethyl or propyl, are attached to a linear alkyl chain. The alkyl can be substituted by one or more substituents independently selected from the group consisting of halo, aryl, cycloalkyl, cyano, hydroxy, alkoxy, alkylthio, amino, —NH(alkyl), —NH(cycloalkyl), —N(alkyl)$_2$ (which alkyls can be the same or different), carboxy and —C(O)O-alkyl. Non-limiting examples of suitable alkyl groups include methyl, ethyl, n-propyl, isopropyl, n-butyl, t-butyl, n-pentyl, heptyl, nonyl, decyl, fluoromethyl, trifluoromethyl and cyclopropylmethyl.

"Alkenyl" means an aliphatic hydrocarbon group (straight or branched carbon chain) comprising one or more double bonds in the chain and which can be conjugated or unconjugated. Useful alkenyl groups can comprise 2 to about 15 carbon atoms in the chain, preferably 2 to about 12 carbon atoms in the chain, and more preferably 2 to about 6 carbon atoms in the chain. The alkenyl group can be substituted by one or more substituents independently selected from the group consisting of halo, alkyl, aryl, cycloalkyl, cyano and alkoxy. Non-limiting examples of suitable alkenyl groups include ethenyl, propenyl, n-butenyl, 3-methylbut-enyl and n-pentenyl.

Where an alkyl or alkenyl chain joins two other variables and is therefore bivalent, the terms alkylene and alkenylene, respectively, are used.

"Alkoxy" means an alkyl-O— group in which the alkyl group is as previously described. Useful alkoxy groups can comprise 1 to about 12 carbon atoms, preferably 1 to about 6 carbon atoms. Non-limiting examples of suitable alkoxy groups include methoxy, ethoxy and isopropoxy. The alkyl group of the alkoxy is linked to an adjacent moiety through the ether oxygen.

"Alkynyl" means an aliphatic hydrocarbon group comprising at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. Non-limiting examples of suitable alkynyl groups include ethynyl, propynyl, 2-butynyl, 3-methylbutynyl, n-pentynyl, and decynyl. The alkynyl group may be substituted by one or more substituents which may be the same or different, each substituent being independently selected from the group consisting of alkyl, aryl and cycloalkyl.

"Aryl" means an aromatic monocyclic or multicyclic ring system comprising about 5 to about 14 carbon atoms, preferably about 6 to about 10 carbon atoms. The aryl can be substituted with one or more substituents, as defined above, which may be the same or different. Non-limiting examples of suitable aryl groups include phenyl, naphthyl, indenyl, tetrahydronaphthyl and indanyl. "Arylene" means a bivalent phenyl group, including ortho, meta and para-substitution.

The term "Boc" refers to N-tert-butoxycarbonyl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be substituted with one or more substituents, as defined above, which may be the same or different. Non-limiting examples of suitable monocyclic cycloalkyls include cyclopropyl, cyclobutyl, cyclopentyl, cyclohexyl and the like. Non-limiting examples of suitable multicyclic cycloalkyls include 1-decalinyl, norbornyl, adamantyl and the like. "Cycloalkylene" refers to a corresponding bivalent ring, wherein the points of attachment to other groups include all positional isomers.

"Dihydroxy($C_1$–$C_6$)alkyl" refers to an alkyl chain substituted by two hydroxy groups on two different carbon atoms.

"Fluoroalkyl", "difluoroalkyl" and "trifluoroalkyl" mean alkyl chains wherein the terminal carbon is substituted by 1, 2 or 3 fluoroatoms, respectively, e.g., —$CF_3$, —$CH_2CF_3$, —$CH_2CHF_2$ or —$CH_2CH_2F$.

"Halogen" or "halo" refers to fluorine, chlorine, bromine or iodine radicals. Preferred are fluoro, chloro or bromo, and more preferred are fluoro and chloro.

"Heteroaryl" means a single ring, bicyclic or benzofused heteroaryl group of 5 to 14 ring atoms, preferably about 5 to 10 ring atoms, comprised of 1 to 13 carbon atoms and 1 to 4 heteroatoms independently selected from the group consisting of N, O and S, provided that the rings do not include adjacent oxygen and/or sulfur atoms. N-oxides of the ring nitrogens are also included, as well as compounds wherein a ring nitrogen is substituted by a ($C_1$–$C_4$)alkyl group to form a quaternary amine. Examples of single-ring heteroaryl groups are pyridyl, oxazolyl, isoxazolyl, oxadiazolyl, furanyl, pyrrolyl, thienyl, imidazolyl, pyrazolyl, tetrazolyl, thiazolyl, isothiazolyl, thiadiazolyl, pyrazinyl, pyrimidyl, pyridazinyl and triazolyl. Examples of bicyclic heteroaryl groups are naphthyridyl (e.g., 1, 5 or 1, 7), imidazopyridyl, pyrido[2,3]imidazolyl, pyridopyrimidinyl and 7-azaindolyl. Examples of benzofused heteroaryl groups are indolyl, quinolyl, isoquinolyl, phthalazinyl, benzothienyl (i.e., thionaphthenyl), benzimidazolyl, benzofuranyl, benzoxazolyl and benzofurazanyl. All positional isomers are contemplated, e.g., 2-pyridyl, 3-pyridyl and 4-pyridyl.

The term "Het" is exemplified by the single ring, bicyclic and benzofused heteroaryl groups as defined immediately above. Het groups are joined to group B by a carbon ring member, e.g., Het is 2-pyridyl, 3-pyridyl or 2-quinolyl. The Het ring can be substituted on any available ring carbon by a group W; 1 to 4 W substituents can be present on a Het ring.

"Heterocycloalkyl" means a 4 to 6 membered saturated ring containing 3 to 5 carbon atoms and 1 or 2 heteroatoms selected from the group consisting of N, S and O, provided that the heteroatoms are not adjacent. Examples of heterocycloalkyl rings are pyrrolidinyl, piperidinyl, piperazinyl, morpholinyl, thiomorpholinyl, thiazolidinyl, 1,3-dioxolanyl, 1,4-dioxanyl, tetrahydrofuranyl, tetrahydrothiophenyl and tetrahydrothiopyranyl.

The term "heterospirocyclic" refers to a spirocyclic structure containing 3 to 5 carbon atoms and 1 or 2 heteroatoms selected from the group consisting of N, S and O, provided that the heteroatoms are not adjacent.

The term "optional single bond" refers to the bond shown by the dotted line between X and the carbon to which Y and $R^{15}$ are attached in the structure of Formula I. The optional double bond represented by -----means that at least a single bond must be present, but that a double bond can be present; when the double bond is present, $R^{10}$ is absent.

When $R^4$ and $R^5$ join to form a ring with the nitrogen to which they are attached, the rings formed are 1-pyrrolidinyl, 1-piperidinyl and 1-piperazinyl, wherein the piperazinyl ring may also be substituted at the 4-position nitrogen by a group $R^7$.

The above statements, wherein, for example, $R^4$ and $R^5$ are said to be independently selected from a group of substituents, means that $R^4$ and $R^5$ are independently selected when attached to the same nitrogen, but also that where an $R^4$ or $R^5$ variable occurs more than once in a molecule, those occurrences are independently selected. Similarly, each occurrence of $R^{13}$ or $R^{14}$ is independent of any other $R^{13}$ or $R^{14}$ in the same Q ring. Those skilled in the art will recognize that the size and nature of the substituent(s) will affect the number of substituents which can be present.

Compounds of the invention have at least one asymmetrical carbon atom and therefore all isomers, including enantiomers, stereoisomers, rotamers, tautomers and racemates of the compounds of Formula (I) (where they exist) are contemplated as being part of this invention. The invention includes d and l isomers in both pure form and in admixture, including racemic mixtures. Isomers can be prepared using conventional techniques, either by reacting optically pure or optically enriched starting materials or by separating isomers of a compound of Formula I. Isomers may also include geometric isomers, e.g., when a double bond is present. Polymorphous forms of the compounds of Formula (I), whether crystalline or amorphous, also are contemplated as being part of this invention.

Those skilled in the art will appreciate that for some of the compounds of Formula I, one isomer will show greater pharmacological activity than other isomers.

Typical preferred compounds of the present invention have the following stereochemistry:

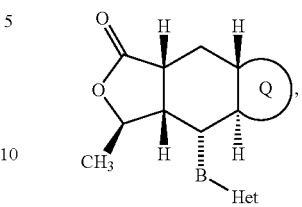

with compounds having that absolute stereochemistry being more preferred.

Those skilled in the art will appreciate that for some compounds of Formula I, one isomer will show greater pharmacological activity than other isomers.

Compounds of the invention with a basic group can form pharmaceutically acceptable salts with organic and inorganic acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. Preferred embodiments include bisulfate salts. The salt is prepared by contacting the free base form with a sufficient amount of the desired acid to produce a salt. The free base form may be regenerated by treating the salt with a suitable dilute aqueous base solution such as dilute aqueous sodium bicarbonate. The free base form differs from its respective salt form somewhat in certain physical properties, such as solubility in polar solvents, but the salt is otherwise equivalent to its respective free base forms for purposes of the invention. Compounds of the invention can also form pharmaceutically acceptable solvates, including hydrates.

Certain compounds of the invention are acidic (e.g., those compounds which possess a carboxyl group). These compounds form pharmaceutically acceptable salts with inorganic and organic bases. Examples of such salts are the sodium, potassium, calcium, aluminum, lithium, gold and silver salts. Also included are salts formed with pharmaceutically acceptable amines such as ammonia, alkyl amines, hydroxyalkylamines, N-methylglucamine and the like.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

Compounds of the present invention in which $n_6$ is 0 can be prepared by processes known in the art, for example by the processes described in U.S. Pat. No. 6,063,847, incorporated herein by reference, and by the processes exemplified below.

Compounds of the present invention in which $n_6$ is 1 or 2 are generally prepared by processes in accordance with the following general scheme:

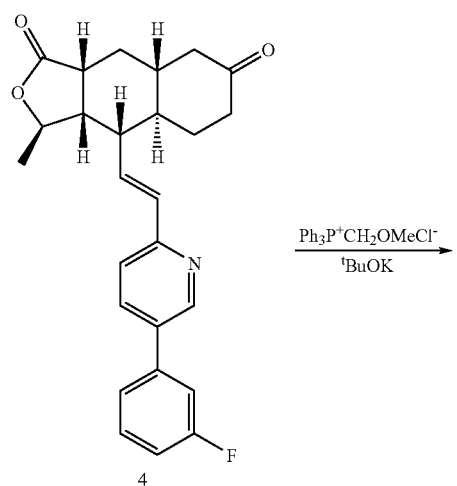
4
Ph₃P⁺CH₂OMeCl⁻
ᵗBuOK
→
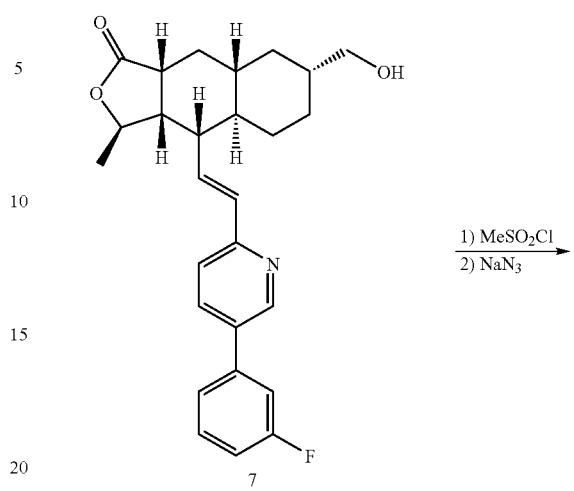
7
1) MeSO₂Cl
2) NaN₃
→
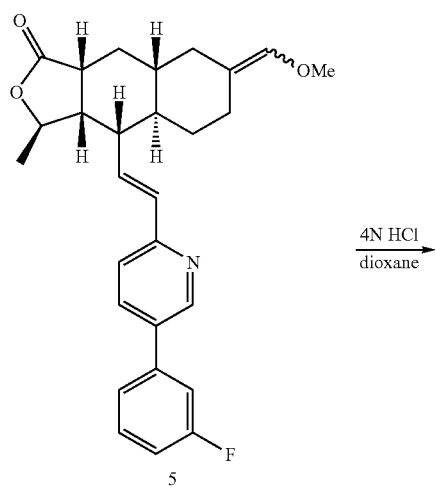
5
4N HCl
dioxane
→
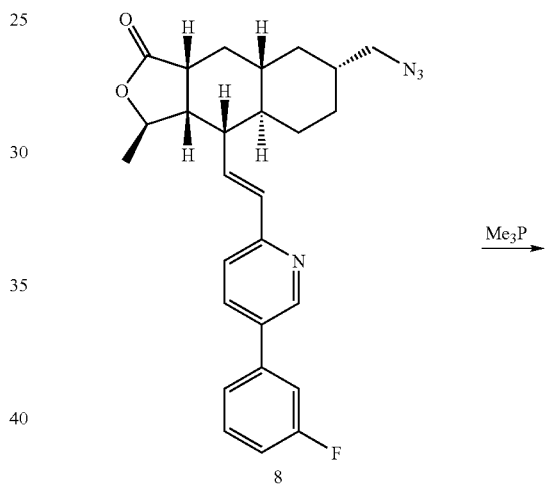
8
Me₃P
→
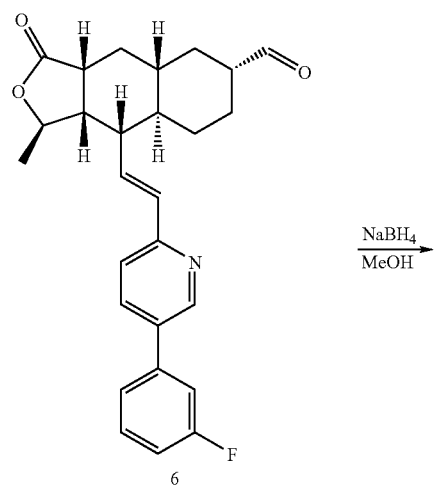
6
NaBH₄
MeOH
→
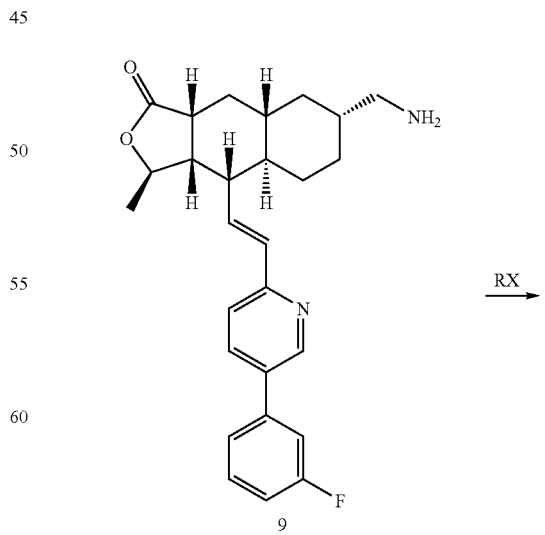
9
RX
→

-continued

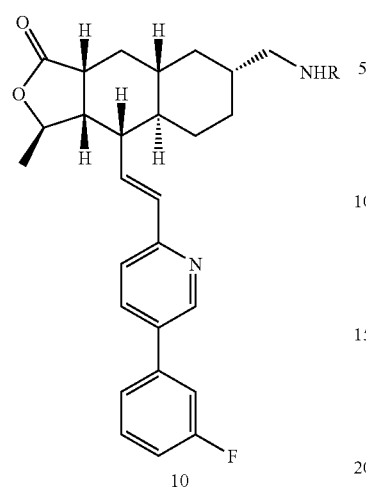

Ketone 4 is subjected to a Wittig reaction to provide vinyl ether 5 which is hydrolyzed under acidic condition to provide aldehyde 6. The aldehyde is reduced to the alcohol 7 and converted to azide 8 via its mesylate. Reduction of the azido group with Me₃P provides the amine 9 which is treated with different electrophiles to provide diverse analogs.

Following are examples of preparing compounds of Formula I. In the examples, the following abbreviations are used: Et (ethyl); Me (methyl); Pr (propyl); Ac (acetyl); rt (room temperature); PTLC (preparative thin layer chromatography); THF (tetrahydrofuran); TBAF (tetra-n-butylammonium fluoride); Tips (triisopropylsilyl); and Tf (trifluoromethanesulfonyl).

EXAMPLE 1

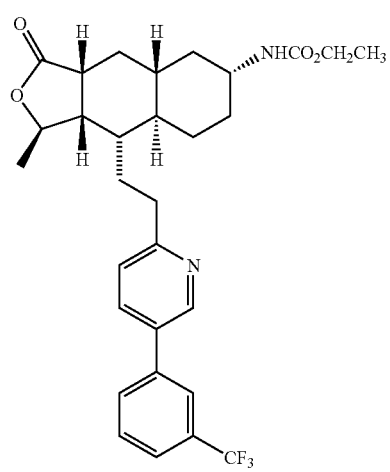

-continued

Step 1:

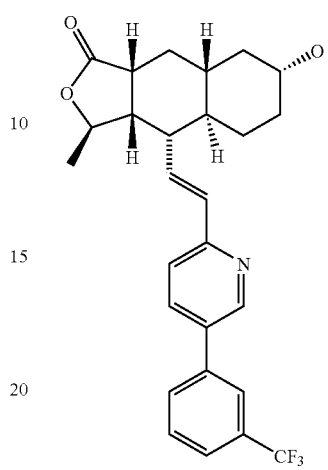

Ti(OiPr)₄
TiCl₄, NH₃
EtOH, CH₂Cl₂
―――――――→
NaBH₃CN
MeOH

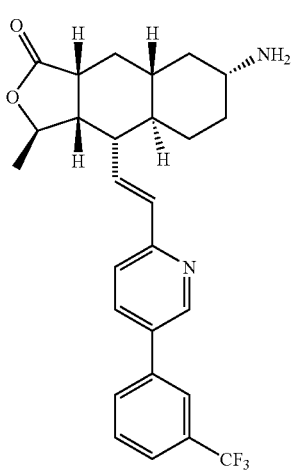

α-2

+

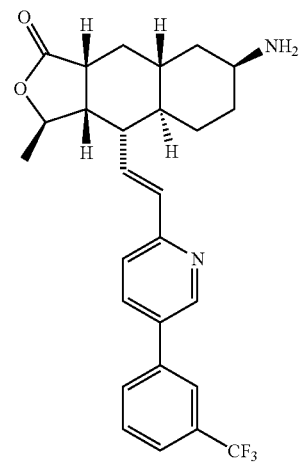

β-2

Compound 1, described in U.S. Pat. No. 6,063,847, (1.95 g, 4.2 mmol) was dissolved in EtOH (40 ml) and CH₂Cl₂ (10 ml). Then, NH₃ (g) was bubbled into the solution for 5 min. The reaction mixture was C(O)Oled to 0° C., and Ti(OiPr)₄ (1.89 ml, 6.3 mmol) was added. After stirring at 0° C. for 1 h, 1M TiCl₄ (6.3 ml, 6.3 mmol) was added. The reaction mixture was stirred at rt for an additional 45 min and concentrated to dryness under reduced pressure. The residue was dissolved in CH₃OH (10 ml) and NaBH₃CN (510 mg, 8 mmol) was added. The resulting suspension was stirred overnight at rt. The reaction mixture was poured to 1 N NaOH (100 ml) and extracted with EtOAc (3×100 ml). The organic layer was combined and dried with Na₂SO₄. Removal of solvent afforded product 2 (1.2 g, 62%). Further separation by PTLC (5% 2 M NH₃ in CH₃OH/CH₂Cl₂) afforded β-2 (spot 1) and α-2 (spot 2) in a 1:2 ratio. β-2: ¹HNMR (CDCl₃): δ 0.81–1.15 (m, 2H), 1.11–1.38 (m, 4H), 1.42 (d, J=6 Hz, 3H), 1.82–2.01 (m, 3H), 2.37 (m, 2H), 2.45 (br m, 1H), 2.65 (m, 1H), 2.81 (m, 1H), 4.75 (m, 1H), 6.61 (m, 2H), 7.26 (m, 2H), 7.75–7.85 (m, 4H), 8.77 (d, J=1.6 Hz, 1H). α-2: ¹HNMR (CDCl₃): δ 0.95 (m, 1H), 1.10–1.40 (m, 5H), 1.41 (d, J=6 Hz, 3H), 1.52–1.65 (m, 2H), 1.75 (m, 1H), 1.84–2.0 (m, 2H), 2.37 (m, 1H), 2.45 (m, 1H), 2.65 (m, 1H), 3.42 (br s, 1H), 4.70 (m, 1H), 6.61 (m, 2H), 7.26 (m, 2H), 7.75–7.85 (m, 4H), 8.77 (d, J=1.6 Hz, 1H).

Step 2:

Compound α-2 (110 mg), ethyl chloroformate (0.4 ml) and Et₃N (0.5 ml) in CH₂Cl₂ (6 ml) were stirred for 2 h. The reaction mixture was directly separated by PTLC (EtOAc/hexane, 1:1) to afford the title compound (100 mg, 79%). MS m/z 543 (M+1). HRMS Calcd for C₃₀H₃₄N₂O₄F₃ (M+1): 543.2471, found 543.2467.

EXAMPLE 1A

N-Methyl Compound for Comparison

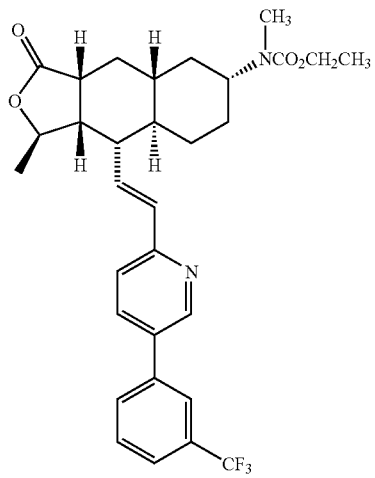

Step 1:

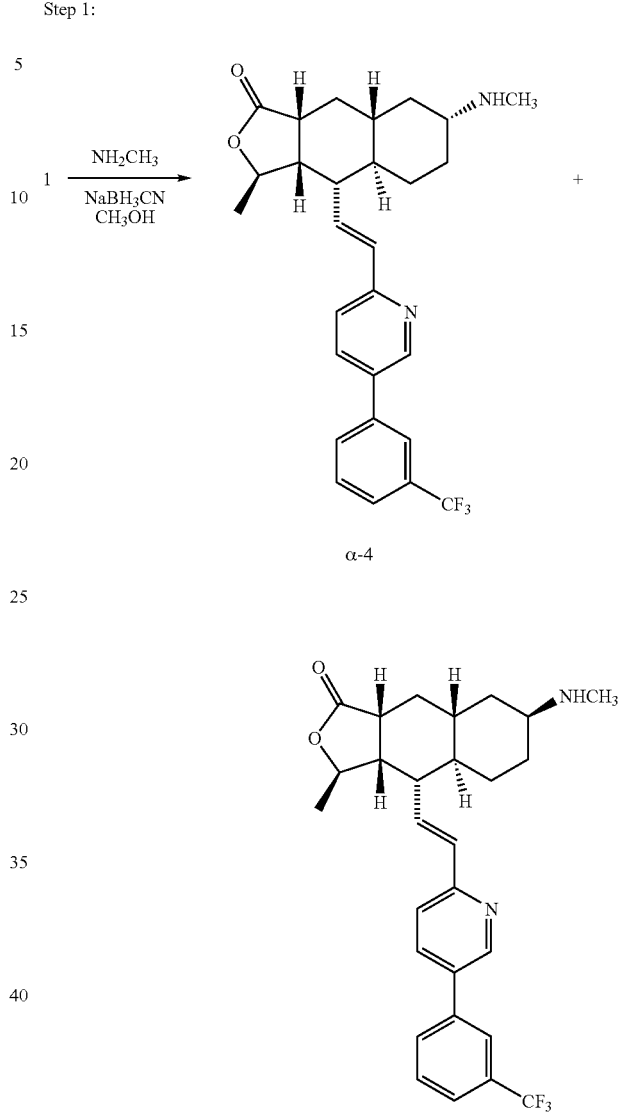

Compound 1 (646 mg, 1.38 mmol) was dissolved in 2.0 M CH₃NH₂ in CH₃OH (15 ml, 30 mmol) and stirred at rt for 5 min followed by addition of NaCNBH₃ (173 mg, 2.75 mmol). The reaction mixture was stirred at rt overnight and concentrated to dryness under reduced pressure. Removal of the solvent followed by PTLC separation (7% 1 M NH₃ in CH₃OH/CH₂Cl₂) afforded β-4 (spot 1, 76 mg, 11%) and α-4 (spot 2, 100 mg, 15%). β-4: ¹HNMR (CDCl₃): δ 1.15–1.24 (m, 5H), 1.42 (d, J=6 Hz, 3H), 1.42–1.61 (m, 2H), 1.71–1.95 (m, 4H), 2.21 (m, 1H), 2.38 (s, 3H), 2.45 (m, 1H), 2.71 (m, 1H), 2.84 (m, 1H), 4.75 (m, 1H), 6.51–6.63 (m, 2H), 7.26 (m, 2H), 7.75–7.85 (m, 4H), 8.77 (d, J=2.0 Hz, 1H). α-4: ¹HNMR (CDCl₃): δ 0.95 (m, 2H), 1.10–1.40 (m, 5H), 1.41 (d, J=6 Hz, 3H), 1.82–1.95 (m, 5H), 2.38 (m, 2H), 2.42 (s, 3H), 2.65 (m, 1H), 4.79 (m, 1H), 6.51–6.63 (m, 2H), 7.26 (m, 2H), 7.75–7.85 (m, 4H), 8.77 (d, J=2.0 Hz, 1H).

Step 2:

Compound α-4 (50 mg), ethyl chloroformate (0.15 ml) and Et₃N (0.3 ml) in CH₂Cl₂ (5 ml) were stirred for 2 h. The reaction mixture was directly separated by PTLC (EtOAc/hexane, 1:1) to afford the title compound (48 mg, 84%). MS m/z 557 (M+1). HRMS Calcd for $C_{31}H_{36}N_2O_4F_3$ (M+1): 557.2627, found 557.2620.

EXAMPLE 2

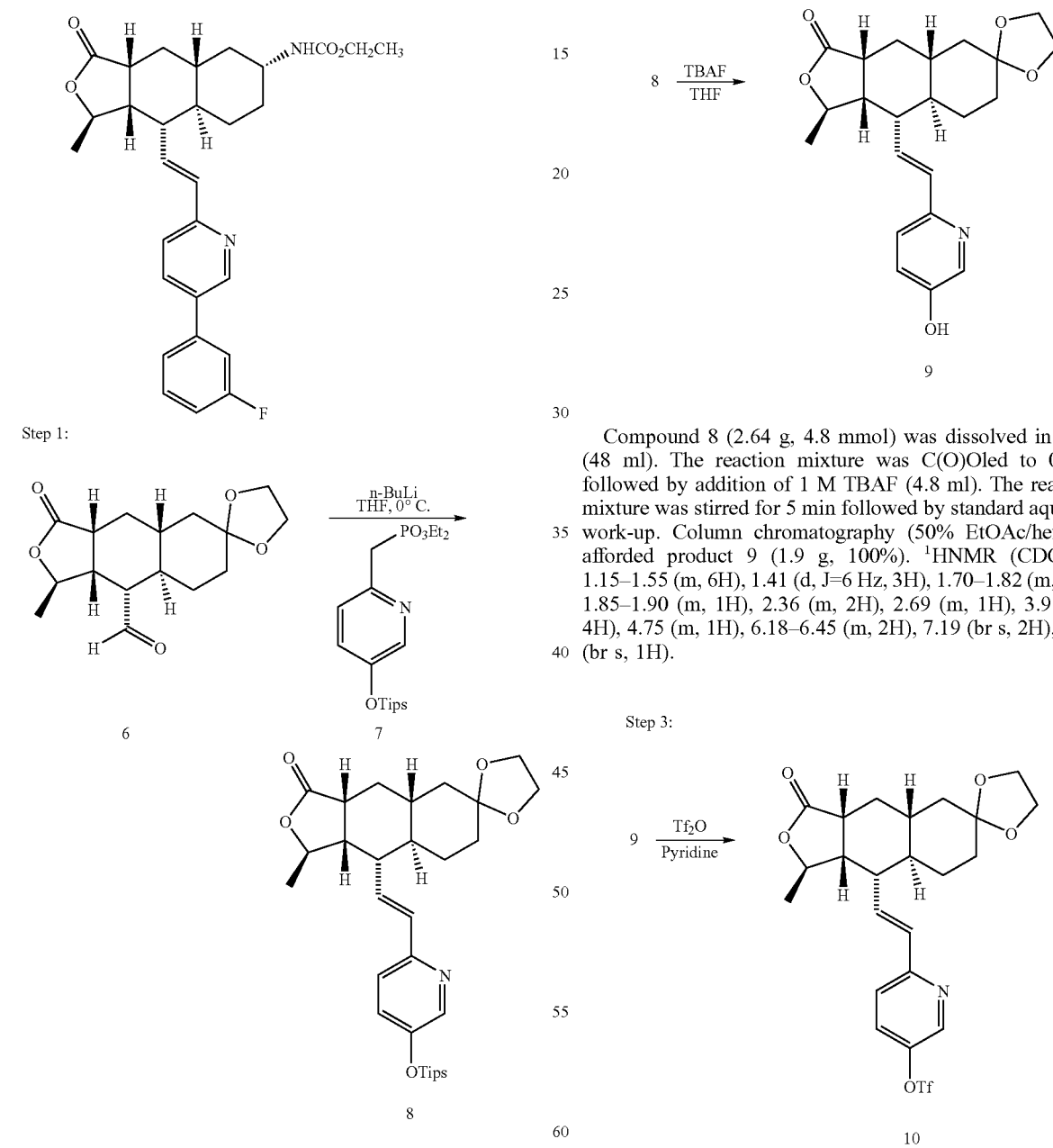

added to the reaction mixture. The reaction mixture was stirred for 30 min. Standard aqueous work-up, followed by column chromatography (30–50% EtOAc in hexane) afforded product 8. ¹HNMR (CDCl₃): δ 0.92–1.38 (m, 31H), 1.41 (d, J=6 Hz, 3H), 1.40–1.55 (m, 2H), 1.70–1.80 (m, 2H), 1.81–1.90 (m, 2H), 2.36 (m, 2H), 2.69 (m, 1H), 3.89 (m, 4H), 4.75 (m, 1H), 6.28–6.41 (m, 2H), 7.05–7.15 (m, 2H), 8.19 (brs, 1H).

Step 2:

Compound 8 (2.64 g, 4.8 mmol) was dissolved in THF (48 ml). The reaction mixture was C(O)Oled to 0° C. followed by addition of 1 M TBAF (4.8 ml). The reaction mixture was stirred for 5 min followed by standard aqueous work-up. Column chromatography (50% EtOAc/hexane) afforded product 9 (1.9 g, 100%). ¹HNMR (CDCl₃):δ 1.15–1.55 (m, 6H), 1.41 (d, J=6 Hz, 3H), 1.70–1.82 (m, 3H), 1.85–1.90 (m, 1H), 2.36 (m, 2H), 2.69 (m, 1H), 3.91 (m, 4H), 4.75 (m, 1H), 6.18–6.45 (m, 2H), 7.19 (br s, 2H), 8.19 (br s, 1H).

Step 3:

Phosphonate 7, described in U.S. Pat. No. 6,063,847, (3.27 g, 8.1 mmol) was dissolved in THF (12 ml) and C(O)Oled to 0° C., followed by addition of 2.5 M n-BuLi (3.2 ml, 8.1 mmol). The reaction mixture was stirred at 0° C. for 10 min and warmed up to rt. A solution of aldehyde 6, described in U.S. Pat. No. 6,063,847, in THF (12 ml) was To a solution of compound 9 (250 mg, 0.65 mmol) in pyridine (5 ml) C(O)Oled to 0° C. was added Tf₂O (295 µL, 2.1 mmol). The reaction mixture was stirred overnight at rt. Standard aqueous work-up followed by column chromatography afforded product 10 (270 mg, 80%). ¹HNMR (CDCl₃): δ 1.15–1.55 (m, 6H), 1.41 (d, J=6 Hz, 3H), 1.70–1.82 (m, 3H), 1.85–1.90 (m, 1H), 2.36 (m, 2H), 2.69 (m, 1H), 3.91 (m, 4H), 4.75 (m, 1H), 6.42–6.68 (m, 2H), 7.25 (m, 1H), 7.55 (m, 1H), 8.49 (d, J=2.8 Hz, 1H).

Step 4:

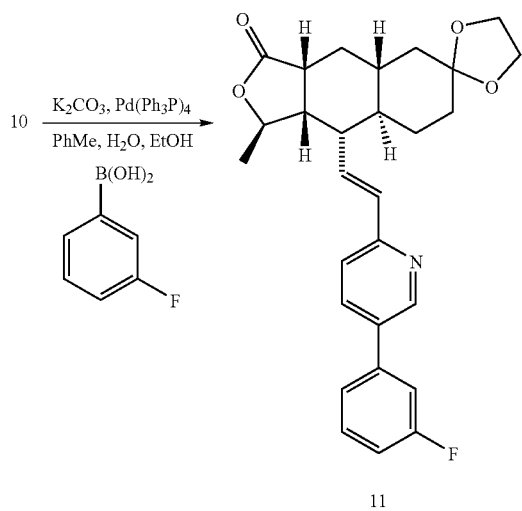

Compound 10 (560 mg, 1.1 mmol), 3-fluorophenyl boronic acid (180 mg, 1.3 mmol) and K₂CO₃ (500 mg, 3.6 mmol) were mixed with toluene (4.4 ml), H₂O (1.5 ml) and EtOH (0.7 ml) in a sealed tube. Under an atmosphere of N₂, Pd(Ph₃P)₄ (110 mg, 0.13 mmol) was added. The reaction mixture was heated at 100° C. for 2 h under N₂. The reaction mixture was C(O)Oled down to rt, poured to EtOAc (30 ml) and washed with water (2×20 ml). The EtOAc solution was dried with NaHCO₃ and concentrated at reduced pressure to give a residue. Preparative TLC separation of the residue (50% EtOAc in hexane) afforded product 11 (445 mg, 89%). ¹HNMR (CDCl₃): δ 1.15–1.59 (m, 6H), 1.43 (d, J=6 Hz, 3H), 1.70–1.79 (m, 2H), 1.82 (m, 1H), 1.91 (m, 2H), 2.41 (m, 2H), 2.69 (m, 1H), 3.91 (m, 4H), 4.75 (m, 1H), 6.52–6.68 (m, 2H), 7.15 (m, 1H), 7.22 (m, 2H), 7.35 (m, 1H), 7.44 (m, 1H), 7.81 (m, 1H), 8.77 (d, J=1.2 Hz, 1H).

Step 5:

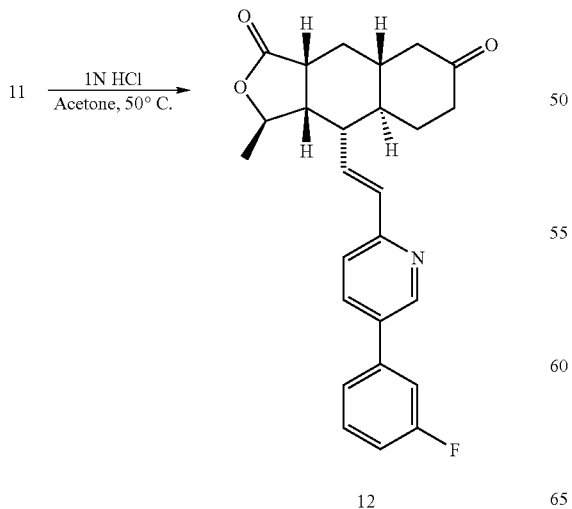

Compound 11 (445 mg, 0.96 mmol) was dissolved in a mixture of acetone (10 ml) and 1 N HCl (10 ml). The reaction mixture was heated at 50° C. for 1 h. Standard aqueous work-up followed by preparative TLC separation (50% EtOAc in hexane) afforded product 12 (356 mg, 89%). ¹HNMR (CDCl₃): δ 1.21–1.45 (m, 2H), 1.47 (d, J=5.6 Hz, 3H), 1.58–1.65 (m, 2H), 2.15 (m, 1H), 2.18–2.28 (m, 2H), 2.35–2.51 (m, 5H), 2.71 (m, 1H), 4.79 (m, 1H), 6.52–6.68 (m, 2H), 7.15 (m, 1H), 7.22 (m, 2H), 7.35 (m, 1H), 7.44 (m, 1H), 7.81 (m, 1H), 8.77 (d, J=1.2 Hz, 1H).

Step 6:

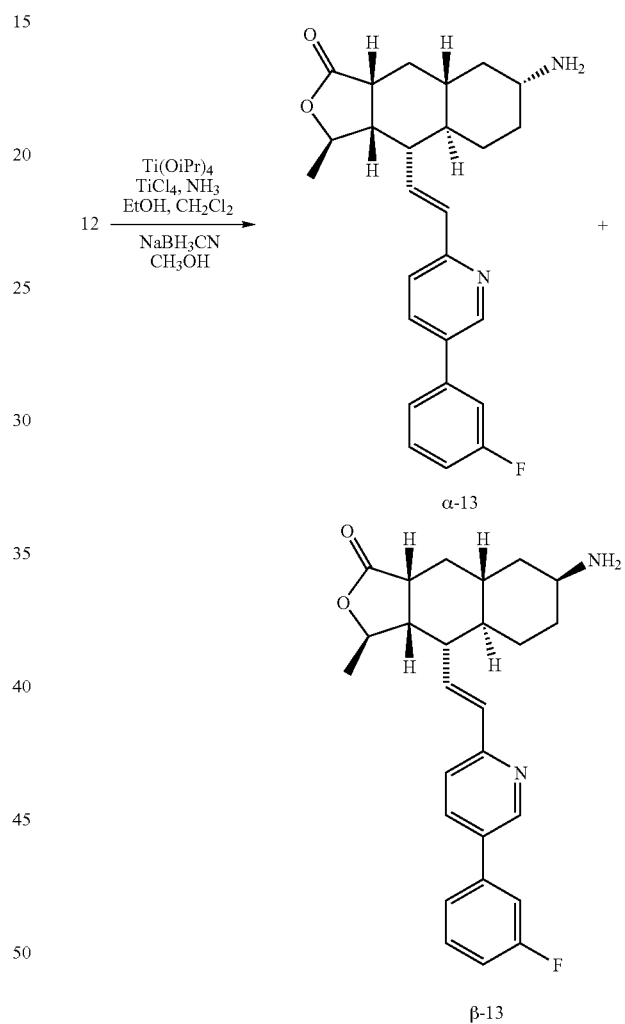

Compound 12 (500 mg, 4.2 mmol) was dissolved in EtOH (40 ml) and CH₂Cl₂ (15 ml) NH₃ (g) was bubbled into the solution for 5 min. The reaction mixture was C(O)Oled to 0° C. followed by addition of Ti(OiPr)₄ (1.89 ml, 6.3 mmol). After stirring at 0° C. for 1 h, 1M TiCl₄ (6.3 ml, 6.3 mmol) was added. The reaction mixture was stirred at rt for 45 min and concentrated to dryness under reduced pressure. The residue was dissolved in CH₃OH (10 ml) and NaBH₃CN (510 mg, 8 mmol) was added. The reaction mixture was stirred overnight at rt. The reaction mixture was poured to 1 N NaOH (100 ml) and extracted with EtOAc (3×100 ml). The organic layer was combined and dried with NaHCO₃. Removal of solvent and separation by PTLC (5% 2 M NH₃ in CH₃OH/CH₂Cl₂) afforded β-13 (spot 1, 30 mg, 6%) and α-13 (spot 2, 98 mg, 20%). β-13: ¹HNMR (CDCl₃): δ 1.50–1.38 (m, 5H), 1.42 (d, J=6 Hz, 3H), 1.51–1.75 (m, 5H), 1.84 (m, 2H), 2.38 (m, 1H), 2.45 (m, 1H), 3.38 (br s, 1H), 4.78 (m, 1H), 6.59 (m, 2H), 7.15 (m, 1H), 7.26 (m, 2H), 7.36 (m, 1H), 7.42 (m, 1H), 7.82 (m, 1H), 8.77 (d, J=2 Hz, 1H). α-13: ¹HNMR (CDCl₃): δ 0.95 (m, 2H), 1.02–1.35 (m, 6H), 1.41 (d, J=6 Hz, 3H), 1.82–1.95 (m, 4H), 2.37 (m, 2H), 2.69 (m, 2H), 4.71 (m, 1H), 6.71 (m, 2H), 7.11 (m, 1H), 7.25 (m, 2H), 7.38 (m, 1H), 7.42 (m, 1H), 7.80 (m, 1H), 8.76 (d, J=1.6 Hz, 1H).

Step 7:

Compound α-13 (300 mg, 0.71 mmol) was dissolved in CH₂Cl₂ (10 ml) followed by addition of Et₃N (0.9 ml). The reaction mixture was C(O)Oled to 0° C. and ethyl chloroformate (0.5 ml) was added. The reaction mixture was stirred at rt for 1 h. The reaction mixture was directly separated by preparative TLC (EtOAc/hexane, 1:1) to give the title compound (14) (300 mg, 86%). MS m/z 493 (M+1). HRMS Calcd for C₂₉H₃₄N₂O₄F (M+1): 493.2503, found 493.2509.

EXAMPLE 2A

N-Methyl Compound for Comparison

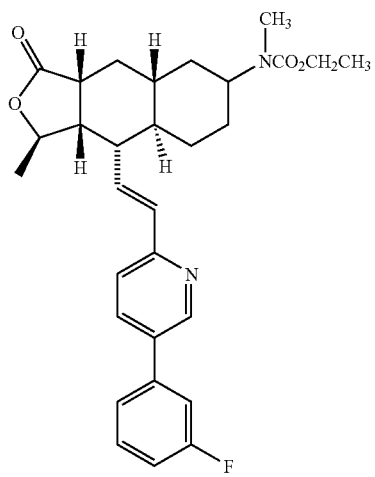

Step 1:

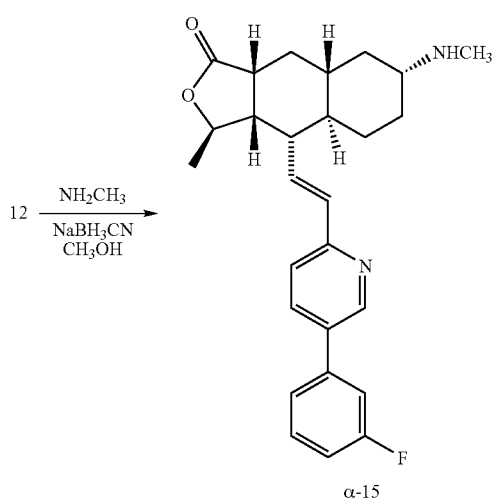

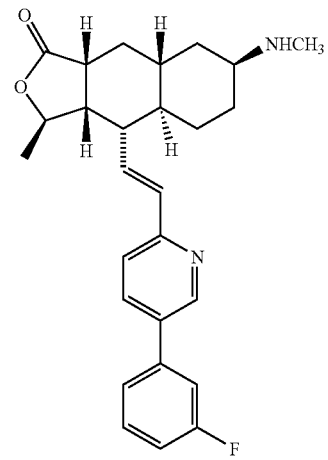

β-15

Compound 12 (130 mg, 0.31 mmol) was dissolved in 2.0 M CH₃NH₂ in CH₃OH (5 ml, 10 mmol). After stirring at rt for 5 min, NaCNBH₃ (40 mg, 0.62 mmol) was added. The reaction mixture was stirred at rt overnight. Removal of the solvent followed by PTLC separation (7% 1 M NH₃ in CH₃OH/CH₂Cl₂) afforded β-15 (spot 1, 20 mg, 15%) and α-15 (spot 2, 25 mg, 19%). β-15: ¹HNMR (CDCl₃): δ 1.15–1.25 (m, 5H), 1.42 (m, 3H), 1.42–1.61 (m, 2H), 1.75–1.90 (m, 3H), 2.25–2.45 (m, 2H), 2.41 (s, 3H), 2.70 (m, 1H), 2.85 (m, 1H), 4.75 (m, 1H), 6.51–6.61 (m, 2H), 7.11 (m, 1H), 7.23–7.27 (m, 2H), 7.35 (m, 1H), 7.45 (m, 1H), 7.80 (m, 1H), 8.76 (d, J=2.4 Hz, 1H). α-15: ¹HNMR (CDCl₃): δ 0.90 (m, 2H), 1.10–1.35 (m, 5H), 1.41 (d, J=5.6 Hz, 3H), 1.82–2.01 (m, 4H), 2.36 (m, 2H), 2.39 (s, 3H), 2.55–2.65 (br s, 1H), 2.71 (m, 1H), 4.79 (m, 1H), 6.51–6.63 (m, 2H), 7.08 (m, 1H), 7.26 (m, 2H), 7.34 (m 1H), 7.42 (m, 1H), 7.81 (m, 1H), 8.76 (d, J=2.0 Hz, 1H).

Step 2:

Compound α-15 (25 mg, 0.06 mmol) was dissolved in CH₂Cl₂ (5 ml) followed by addition of Et₃N (0.2 ml). The reaction mixture was C(O)Oled to 0° C. and ethyl chloroformate (0.1 m) was added. The reaction mixture was stirred at rt for 1 h. The reaction mixture was directly separated by preparative TLC (EtOAc/hexane, 1:1) to give the title compound (25 mg, 85%). MS m/z 507 (M+1). HRMS Calcd for C₃₀H₃₆N₂O₄F (M+1): 507.2659, found 507.2652.

EXAMPLE 3

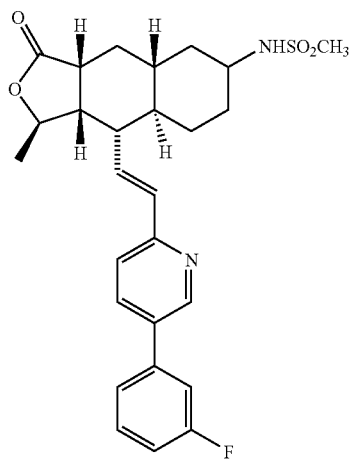

Compound α-13 (10 mg, 0.02 mmol) was dissolved in CH$_2$Cl$_2$ (3 ml) followed by addition of Et$_3$N (0.5 ml). The reaction mixture was C(O)Oled to 0° C. and CH$_3$SO$_2$Cl (0.2 ml) was added. The reaction mixture was stirred at rt for 1 h. The reaction mixture was directly separated by preparative TLC (EtOAc/hexane, 1:1) to give the title compound (10 mg, 84%). MS m/z 499 (M+1). HRMS Calcd for C$_{27}$H$_{32}$N$_2$O$_4$FS (M+1): 499.2067, found 499.2071.

EXAMPLE 4

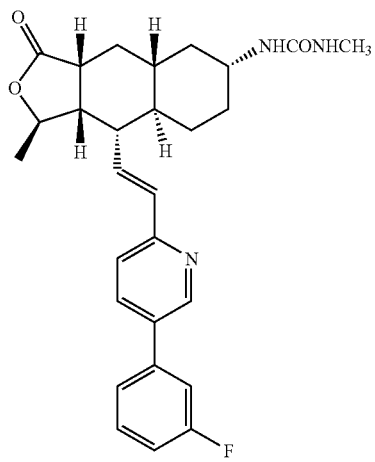

Compound α-13 (50 mg, 0.1 mmol) was dissolved in CH$_2$Cl$_2$ (5 ml) followed by addition of CH$_3$NCO (250 mg). The reaction mixture was stirred at rt for 1 h. The reaction mixture was directly separated by preparative TLC (CH$_3$OH/CH$_2$Cl$_2$, 7%) to give the title compound (60 mg as HCl salt, 98%). MS m/z 478 (M+1). HRMS Calcd for C$_{28}$H$_{33}$N$_3$O$_3$F (M+1): 478.2506, found 478.2516.

EXAMPLE 5

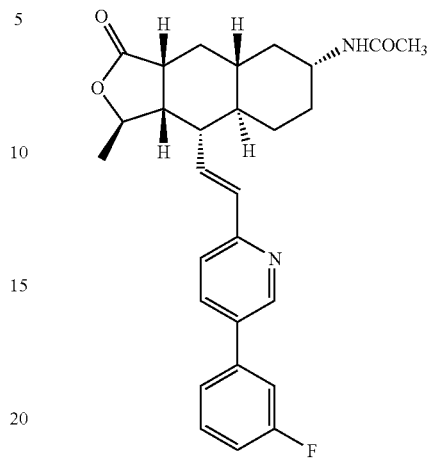

Compound α-13 (50 mg, 0.1 mmol) was dissolved in CH$_2$Cl$_2$ (3 mL) followed by addition of Et$_3$N (0.5 mL). The reaction mixture was C(O)Oled to 0° C. and acetic anhydride (0.2 mL) was added. The reaction mixture was stirred at rt overnight. The reaction mixture was directly separated by preparative TLC (CH$_3$OH/CH$_2$Cl$_2$, 8%) to give the title compound (52 mg, 94%). MS m/z 463 (M+1). HRMS Calcd for C$_{28}$H$_{32}$N$_2$O$_3$F (M+1): 463.2397, found 463.2399.

Using the methods described above, compounds of the following structure were prepared,

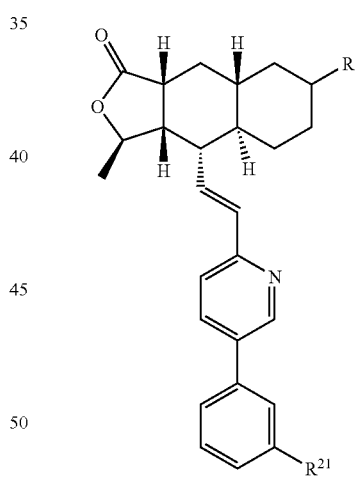

wherein R$^{21}$ and R are as defined in Table 1:

TABLE 1

| Ex. | R$^{21}$ | R | Physical data |
|---|---|---|---|
| 6 | —CF$_3$ | —NHCO$_2$-t-butyl | MS (M + 1): observed: 571 |
| 7 | —CF$_3$ | —NHCO$_2$CH$_3$ | HRMS (M + 1): observed: 529.2323 |
| 8 | —CF$_3$ | —NHCO$_2$CH$_2$CH$_3$ | HRMS (M + 1): observed: 543.2467 |
| 9 | —CF$_3$ | —NHCO$_2$CH$_2$CH$_2$OCH$_3$ | HRMS (M + 1): observed: 573.2569 |
| 10 | H | —NHCO$_2$CH$_2$CH$_3$ | HRMS (M + 1): observed: 475.2592 |

TABLE 1-continued

| Ex. | R[21] | R | Physical data |
|---|---|---|---|
| 11 | F | ◂NHCO₂CH₂CH₃ | HRMS (M + 1): observed: 493.2509 |
| 12* | —CF₃ | —N(n-Pr)CO₂CH₂CH₃ | HRMS (M + 1): observed: 585.2951 |
| 13* | —CF₃ | —N(n-Pr)CO₂CH₂CH₃ | HRMS (M + 1): observed: 585.2951 |
| 14 | —CF₃ | ⋯NHCOCH₃ | HRMS (M + 1): observed: 513.2362 |
| 15 | —CF₃ | ◂NHCOCH₃ | HRMS (M + 1): observed: 513.2367 |
| 16 | F | ⋯NHCOCH₂CH₃ | HRMS (M + 1): observed : 477.2560 |
| 17 | F | ⋯NHC(O)-cyclopropyl | HRMS (M + 1): observed: 489.2557 |
| 18 | F | ◂NHCOCH₃ | HRMS (M + 1): observed: 463.2401 |
| 19 | —CF₃ | —NHCOCH₂OCH₃ | HRMS (M + 1): observed: 543.2465 |
| 20 | —CF₃ | —NHCOCH₂OC(O)CH₃ | HRMS (M + 1): observed: 571.2416 |
| 21 | —CF₃ | —NHCONHCH₂CH₃ | HRMS (M + 1): observed: 542.2636 |
| 22 | —CF₃ | —NHCONHCH₃ | HRMS (M + 1): observed: 556.2795 |
| 23 | F | ◂NHCONHCH₃ | HRMS (M + 1): observed: 478.2511 |
| 24 | F | —NHCONHCH₂CH₃ | HRMS (M + 1): observed: 492.2669 |
| 25 | F | ◂NHCONHCH₂CH₃ | HRMS (M + 1): observed: 492.2668 |
| 26 | —CF₃ | —NHSO₂CH₃ | HRMS (M + 1): observed: 563.2198 |
| 27 | —CF₃ | —NHSO₂CH₂CH₃ | HRMS (M + 1): observed: 549.2024 |
| 28 | —CF₃ | —NHSO₂CH₂CH₂CH₃ | HRMS (M + 1): observed: 577.2352 |
| 29 | H | —NHSO₂CH₃ | HRMS (M + 1): observed: 481.2164 |
| 30 | —CF₃ | ⋯NHSO₂CH₃ | HRMS (M + 1): observed: 549.2026 |
| 31 | F | ⋯NHSO₂CH₂CH₃ | HRMS (M + 1): observed: 513.2217 |

*Comparative example

Replacing the pyridine group of compound 1 with a quinoline group, compounds of the following structure were prepared,

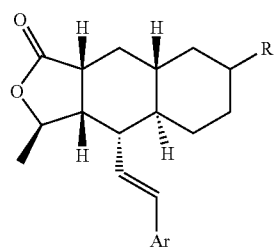

wherein R and Ar are as defined in Table 2:

TABLE 2

| Ex. | Ar | —R | Physical data |
|---|---|---|---|
| 32 | 2-methyl-6-chloroquinolin-?-yl | ⋯NHAc | MS m/z 453 (MH⁺) |
| 33 | 2-methyl-6-chloroquinolin-?-yl | ⋯NHCONHEt | MS m/z 482 (MH⁺) |
| 34 | 2-methyl-6-chloroquinolin-?-yl | ⋯NHCO₂Et | MS m/z 483 (MH⁺) |
| 35 | 2-methyl-6-chloroquinolin-?-yl | ◂NHCO₂Et | MS m/z 483 (MH⁺) |
| 36 | 2-methyl-7-chloroquinolin-?-yl | ◂NHCO₂Et | MS m/z 483 (MH+) |
| 37 | 2-methyl-7-chloroquinolin-?-yl | ⋯NHCO₂Et | MS m/z 483 (MH+) |
| 38 | 2-methyl-7-chloroquinolin-?-yl | ⋯NHAc | MS m/z 453 (MH+) |
| 40 | 2-methyl-8-chloroquinolin-?-yl | ⋯NHAc | MS m/z 453 (MH+) |
| 41 | 2-methyl-8-chloroquinolin-?-yl | ⋯NHCONHEt | MS m/z 482 (MH+) |
| 42 | 2-methyl-8-chloroquinolin-?-yl | ⋯NHCO₂Et | MS m/z 483 (MH+) |
| 43 | 2-methyl-8-chloroquinolin-?-yl | ◂NHCO₂Et | MS m/z 483 (MH+) |

The following analogs were prepared employing further variations of W selected from substituted phenyl and heteroaryl groups:

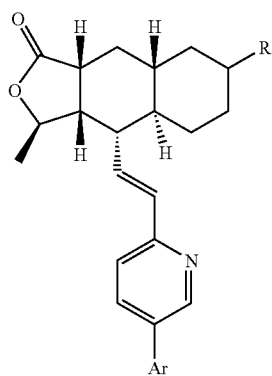

wherein R and Ar are as defined in Table 3:

TABLE 3

| Ex. | Ar | —R | Physical Data |
|---|---|---|---|
| 44 | 2-pyridyl | ·····NHCO₂Et | MS m/z 476 (MH+) |
| 45 | 2-fluorophenyl | ·····NHCO₂Et | MS m/z 493 (MH+) |
| 46 | 3-SMe-phenyl | ·····NHCO₂Et | MS m/z 521 (MH+) |
| 47 | 6-OMe-3-pyridyl | ·····NHCO₂Et | MS m/z 506 (MH+) |
| 48 | 1-methyl-pyrimidinyl | ·····NHCO₂Et | MS m/z 477 (MH+) |
| 49 | 2-pyridyl | ·····NHCO₂Et | MS m/z 476 (MH+) |
| 50 | 3-CONH₂-phenyl | ·····NHCO₂Et | MS m/z 518 (MH+) |
| 51 | 4-pyridyl | ·····NHCO₂Et | MS m/z 476 (MH+) |

TABLE 3-continued

| Ex. | Ar | —R | Physical Data |
|---|---|---|---|
| 52 | 2-thiazolyl | ·····NHCO₂Et | MS m/z 482 (MH+) |
| 53 | 3-furyl | ·····NHCO₂Et | MS m/z 465 (MH+) |
| 54 | 2-CN-phenyl | ·····NHCO₂Et | MS m/z 500 (MH+) |
| 55 | 4-pyridyl | ◄NHCO₂Et | MS m/z 476 (MH+) |
| 56 | 2-CN-phenyl | ◄NHCO₂Et | MS m/z 500 (MH+) |
| 57 | 3-CONH₂-phenyl | ◄NHCO₂Et | MS m/z 518 (MH+) |
| 58 | 2-fluorophenyl | ◄NHCO₂Et | MS m/z 493 (MH+) |
| 59 | 3-Cl-phenyl | ◄NHCO₂Et | MS m/z 509 (MH+) |
| 60 | 3-Cl-phenyl | ·····NHCO₂Et | MS m/z 509 (MH+) |
| 61 | 3,5-difluorophenyl | ·····NHCO₂Et | MS m/z 511 (MH+) |
| 62 | 3,5-difluorophenyl | ◄NHCO₂Et | MS m/z 511 (MH+) |

TABLE 3-continued

| Ex. | Ar | —R | Physical Data |
|---|---|---|---|
| 63 | 3-methyl-2-fluorophenyl | ·······NHCO₂CH₂CONH₂ | MS m/z 522 (MH+) |
| 64 | 3-methyl-2-fluorophenyl | ◂NHCO₂CH₂CONH₂ | MS m/z 522 (MH+) |
| 65 | 2-methoxy-3-methylphenyl | ·······NHCO₂Et | MS m/z 505 (MH+) |
| 66 | 2-methoxy-3-methylphenyl | ◂NHCO₂Et | MS m/z 505 (MH+) |
| 67 | 3-methyl-2-fluorophenyl | ·······NHCO₂CH₂CO₂Me | MS m/z 537 (MH+) |
| 68 | 3-methyl-2-fluorophenyl | ·······NHCO₂CH₂CO₂H | MS m/z 523 (MH+) |

EXAMPLE 69

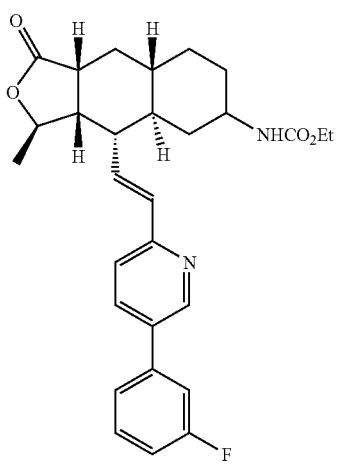

Ex. 69A

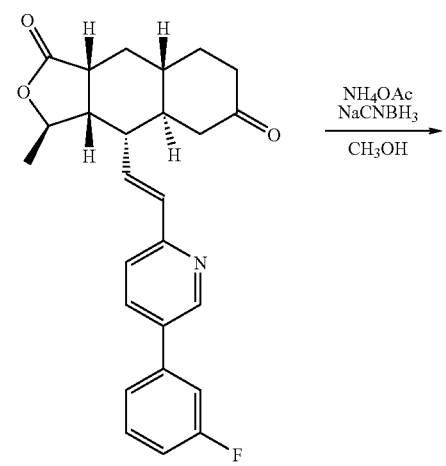

Ex. 69B

Step 1:

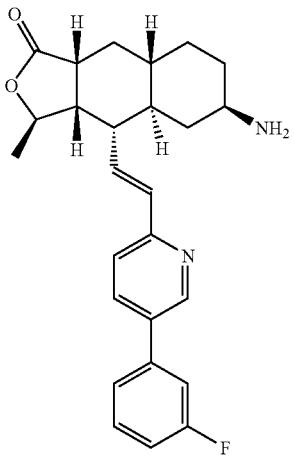

17

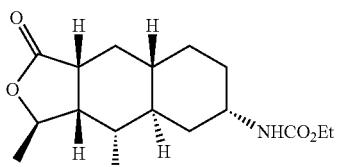

18A

-continued

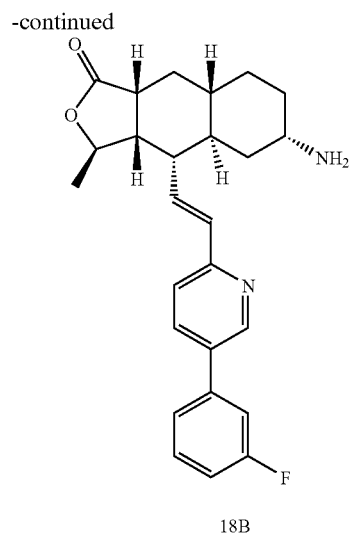

18B

Compound 17 (100 mg, 0.239 mmol), prepared as described in U.S. Pat. No. 6,063,847 was stirred with ammonium acetate (1.84 g, 23.9 mmol) and NaCNBH₃ (24 mg, 0.38 mmol) in CH₃OH (7 ml) at rt under N₂ for 16 h. The mixture was treated with NH₄OH (10 ml, 29% aqueous), diluted with CH₂Cl₂ (75 ml), and washed with NaHCO₃ (sat.). The organic layer was dried (MgSO₄) and concentrated in vacuo. PTLC separation of the residue with 2.0 M NH₃/CH₃OH—CH₂Cl₂ (5–95) as eluent gave 18A (43 mg, 43%, lower R$_f$), MS (ESI) m/z 421 (MH⁺), and 18B (17 mg, 17%, higher R$_f$), MS (ESI) m/z 421 (MH⁺).

Step 2:

Compound 18A (0.100 g, 0.238 mmol) was stirred with ethyl chloroformate (0.195 ml, 2.38 mmol) and Et₃N (0.5 ml, 3.6 mmol) in CH₂Cl₂ (10 ml) at 0° C. for 10 min and at rt for 1 h. The mixture was diluted with EtOAc (50 ml) and washed with NaHCO₃ (sat.). The organic layer was dried (MgSO₄) and concentrated in vacuo. Flash chromatography of the residue on a silica gel column with EtOAc-hexane (50-50) as eluent gave Example 69A (100 mg, 85%). MS (ESI) m/z 493 (MH⁺). Compound 32B was similarly prepared from 18B. MS (ESI) m/z 493 (MH⁺).

EXAMPLE 70

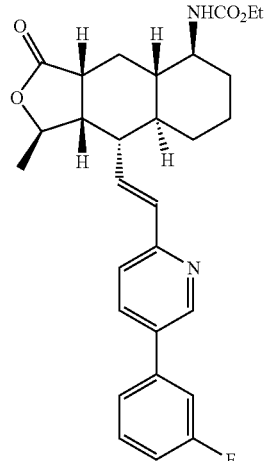

70A

-continued

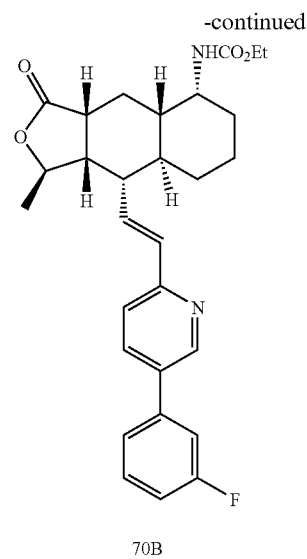

70B

Step 1:

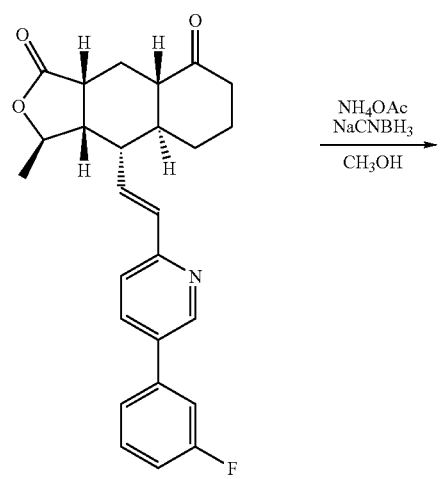

19

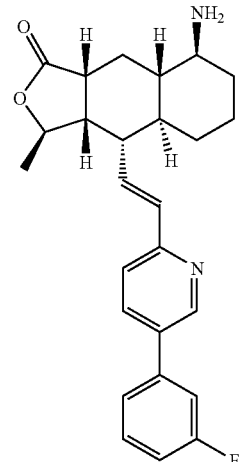

20A

-continued

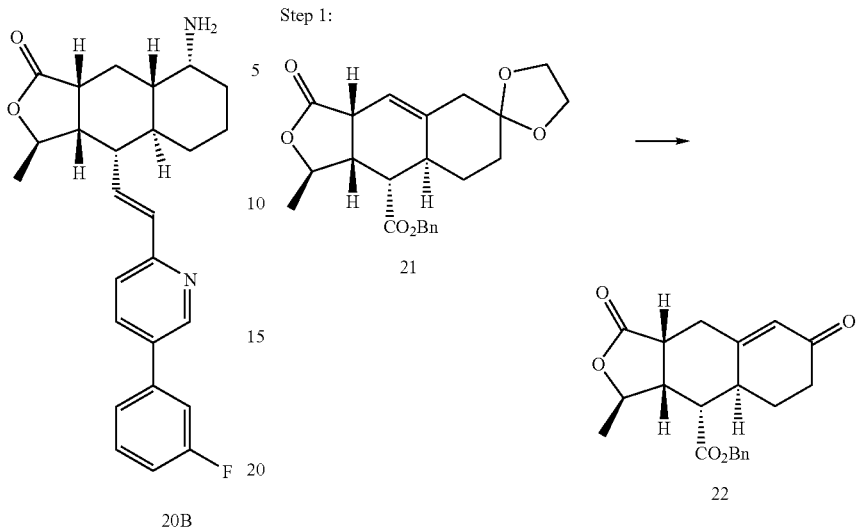
20B

Using the procedure of Example 32, Step 1, starting with compound 19 (see U.S. Pat. No. 6,063,847), prepare: 20A (lower $R_f$), MS (FAB) m/z 421 (MH$^+$), and 20B (higher $R_f$), MS (FAB) m/z 421 (MH$^+$).

Step 2:

Using the procedure of Example 69, Step 2, Example 70A was prepared from compound 20A: MS (ESI) m/z 493 (MH$^+$). Using the procedure of Example 69, Step 2, Example 70B was prepared from compound 20B: MS (ESI) m/z 493 (MH$^+$).

EXAMPLE 71

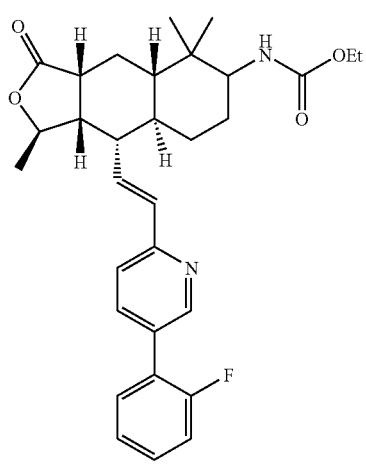

Step 1:

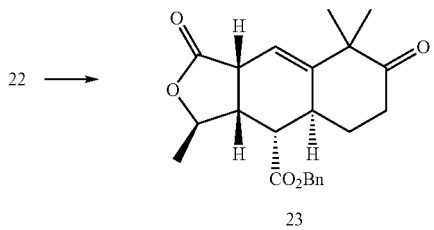

Lactone 21, described in U.S. Pat. No. 6,063,847 (10 g, 0.0251 mol) was dissolved in acetone, 1 N HCl was added and the mixture heated at 55° C. for 4 h. The mixture was allowed to C(O)Ol to rt, neutralized with NaHCO$_3$, and extracted with EtOAc. The extracts were dried and concentrated under reduced pressure to give 22 (7.35 g) as oil. MS m/z 355 (M+1).

Step 2:

22 →

23

Ketone 22 (7.35 g, 0.0207 mol) was dissolved in THF and C(O)Oled to 0° C. Potassium tert-butoxide was added (2.55 g, 1.1 eq). After stirring for 10 min, CH$_3$I (2.58 ml, 2 eq) was added. The mixture was stirred for 2.5 h. Aqueous work-up with NH$_4$Cl$_{(sat)}$ followed by column chromatography (30–50% EtOAc in hexane) gave 23 (1.63 g). MS m/z 383 (M+1).

Step 3:

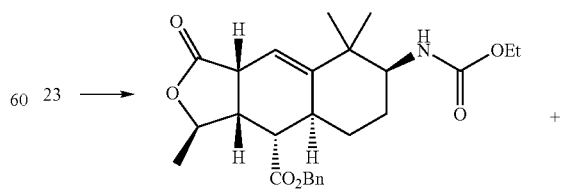
β-24

+

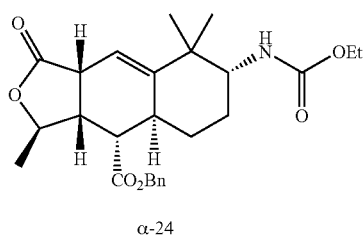

α-24

Ketone 23 (1.634 g, 0.00426 mol) was dissolved in CH$_3$OH, NH$_4$OAc and NaCNBH$_3$ were added. The mixture was stirred for 2 h. The reaction was quenched with NH$_4$OH and the mixture extracted with CH$_2$Cl$_2$. The organic extracts were dried and concentrated to give an oil. MS m/z 383 (M+1).

The oil was dissolved in CH$_2$CO$_2$, Et$_3$N was added and the mixture C(O)Oled to 0° C. Ethyl chloroformate was added and the mixture was stirred overnight. Aqueous work-up with NH$_4$Cl$_{(sat)}$ followed by column chromatography (30% EtOAc in hexane) gave 0.797 g of an inseparable 3:1 mixture of α-24 and β-24. MS m/z 456 (M+1).

Step 4:

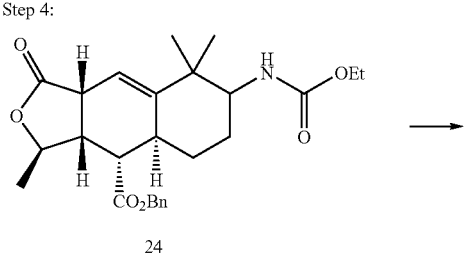

24

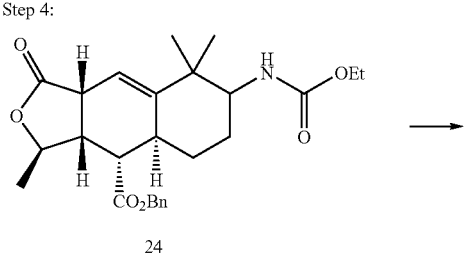

25

The product mixture from step 3 (330 mg, 0.724 mmol) was dissolved in EtOAc (14 ml) and Pd(C) (10% by wt) was added. The mixture was stirred under H$_2$ (1 atm) for 2 h. The mixture was filtered, concentrated, and dissolved in CH$_3$OH (15 ml). PtO$_2$ (10% by wt) was added, the mixture was placed under H$_2$ atmosphere (50 psi), and agitated on a parr shaker for 3 days. The mixture was filtered and concentrated to give 280 mg of acids 25. MS m/z 368 (M+1).

Step 5:

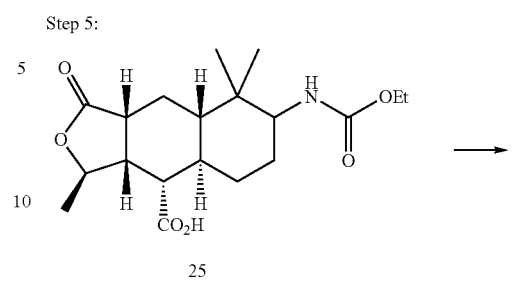

25

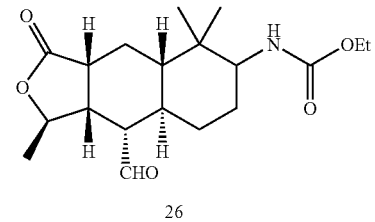

26

The crude acids 25 (0.724 mmol) were dissolved in CH$_2$Cl$_2$. (COCl)$_2$ (0.1 ml, 1.5 eq) and a drop of DMF were added. The mixture was stirred for 30 min, when $^1$H NMR showed complete conversion. The CH$_2$Cl$_2$ was replaced with toluene and the resulting solution was C(O)Oled to 0° C. Pd(Ph$_3$P)$_4$ was added, followed by dropwise addition of Bu$_3$SnH. After stirring at 0° C. for 30 min, TLC showed complete reaction. Column chromatography (20–50% EtOAc in hexane) gave 248 mg of aldehydes 26. MS m/z 352 (M+1).

Step 6:

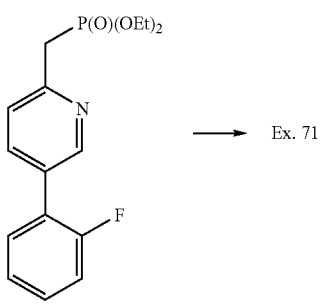

→ Ex. 71

Phosphonate 27 (248 mg, 0.768 mmol, 3 eq), see U.S. Pat. No. 6,063,847, was dissolved in THF (4 ml) and the mixture was C(O)Oled to 0° C. LHMDS (0.768 ml, 3 eq of a 1M solution in THF) was added and the resulting mixture stirred for 30 min. Ti(i-OPr)$_4$ (0.227 ml, 3 eq.) was added and 5 min later a solution of aldehydes 26 (90 mg, 0.256 mol) in THF (4 ml) was added. The mixture was stirred for 1.5 h when TLC showed complete conversion. Saturated sodium potassium tartrate was added and the THF removed under vacuum. The residue was extracted with EtOAc, dried, concentrated and purified by PTLC (1:1 EtOAc/hexane) to give the title compound (80 mg). MS m/z 521 (M+1).

EXAMPLE 72

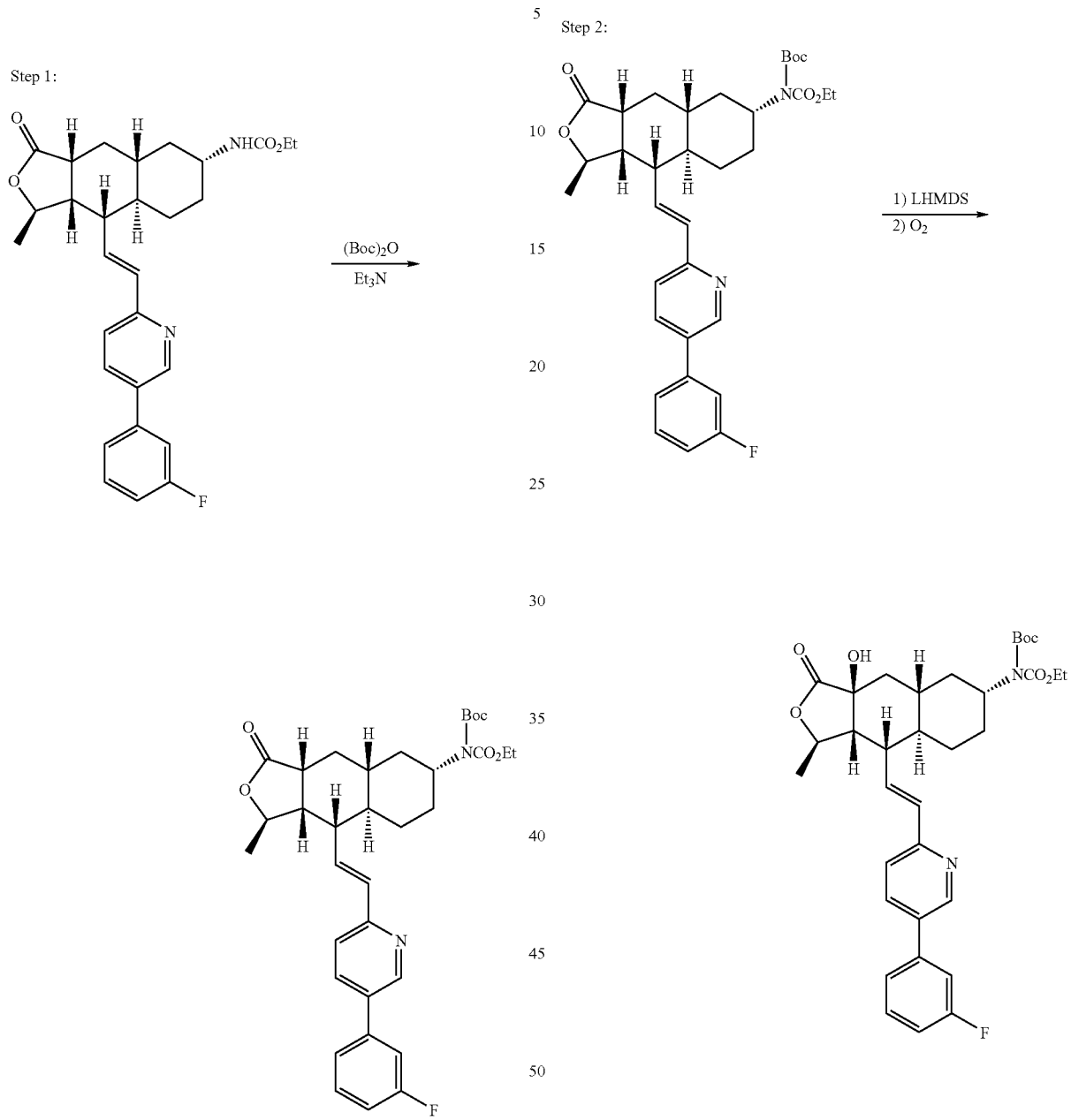

To a solution of 1.35 g (2.75 mmol) of starting material, 0.57 ml of Et₃N (4.13 mmol, 1.5 equiv.) and 70 mg of DMAP (0.57 mmol, 0.2 equiv.) in 20 ml CH₃CN at 60° C. was added 2 equivalents of (Boc)₂O. Subsequently, 5 equivalents of (Boc)₂O was introduced over a period of 5 hr. The solution was C(O)Oled, concentrated and chromatographed to provide 0.86 g of product.

MS: 593.1 (MH⁺)

To a solution of 280 mg (0.47 mmol) of starting material in 5 ml THF at 0° C. was added 0.95 ml (0.95 mmol, 2 equiv.) of 1M LHMDS in THF. The mixture was stirred for 30 min. and O₂ was introduced via a balloon. After stirring for 1 hr, the reaction was quenched with the addition of 50 ml of aq. Na₂SO₃ and stirred for 1 hr. The aqueous layer was extracted with 3×25 ml of ethylacetate and the combined organic layer was washed with brine, dried over MgSO₄ and chromatographed with 30% EtOAc-hexanes to afford 125 mg of hydroxylated product.

MS: 609.1 (MH⁺)

EXAMPLE 73

Step 3:

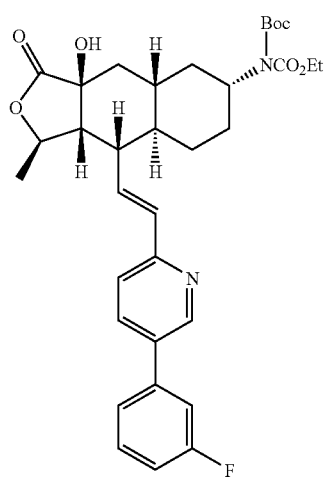 TFA-DCM → 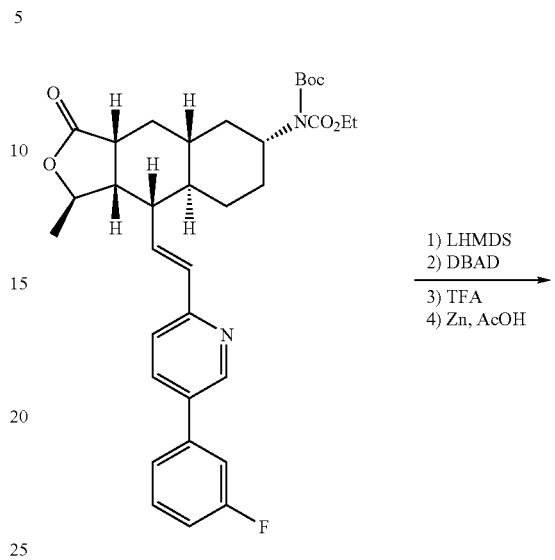

1) LHMDS
2) DBAD
3) TFA
4) Zn, AcOH

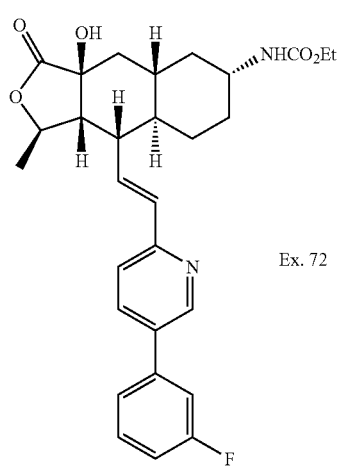

Ex. 72

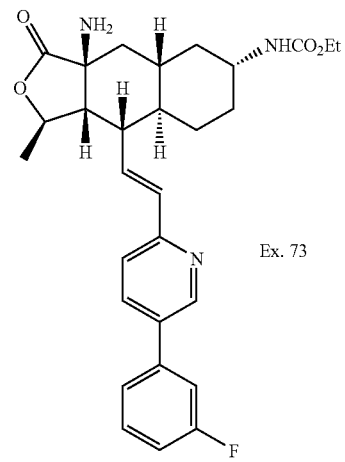

Ex. 73

To a solution of 125 mg of starting material in 1 ml CH$_2$Cl$_2$ at room temperature was added 1 ml of trifluoroacetic acid, stirred for 1 hr and concentrated. To this was added 50 ml of aq. Na$_2$CO$_3$ and extracted with 3×10 ml CH$_2$Cl$_2$. The combined organic layer was washed with 10 ml brine, dried over MgSO$_4$, filtered, concentrated and chromatographed with 50% EtOAc-hexanes to provide 90 mg of product.

HRMS: 509.2459 (MH$^+$)

To a solution of 500 mg (0.84 mmol) of starting material in 8 ml THF was added 1.7 ml (1.7 mmol, 2 equiv.) of 1M LHMDS in THF. The solution was stirred for 30 min. and C(O)Oled to −78° C., and a solution of 390 mg (1.7 mmol, 2 equiv.) di-tert-butyl azodicarboxylate (DBAD) in 2 ml THF was added. The reaction was allowed to warm to room temperature over a period of 3 hr, poured into 100 ml aq. NH$_4$Cl and extracted with 3×30 ml of EtOAc. The combined organic layers were washed with 30 ml brine, dried over MgSO$_4$, filtered and concentrated to provide the crude product.

This was stirred with 15 ml of 1:1 TFA-DCM at room temperature for 1 hr, concentrated and basified with 100 ml of aq. Na$_2$CO$_3$. The aqueous layer was extracted with 3×25 ml of DCM, combined organic layers were washed with 25 ml brine, dried over MgSO$_4$, filtered and concentrated to provide the crude hydrazide.

The crude hydrazide was dissolved in 10 ml of glacial acetic acid and 2 g of Zn powder was added in small portions and stirred for about 1.5 hr. It was filtered through celite and rinsed with 100 ml of DCM. The DCM solution was washed with 2×50 ml H$_2$O, 2×50 ml aq. NaHCO$_3$, 50 ml brine, dried over MgSO$_4$, filtered, concentrated and chromatographed with 87:10:3 DCM-acetone-MeOH to provide 105 mg of product.

HRMS: 508.2607 (MH$^+$)

EXAMPLE 74

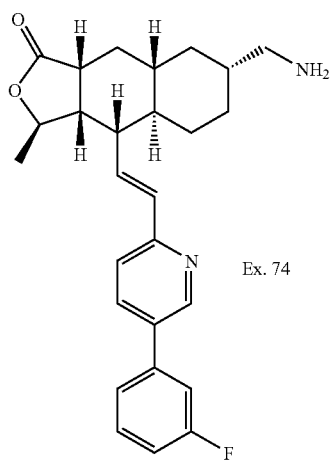

Ex. 74

Step 1:

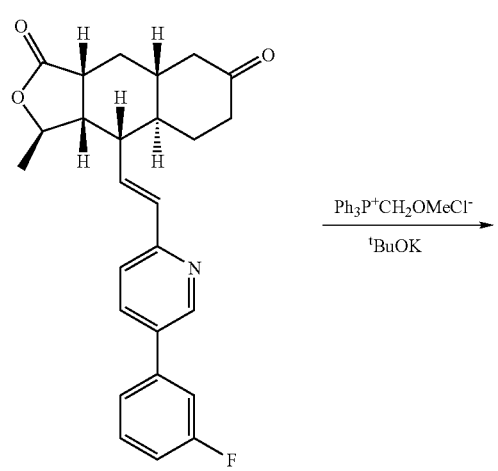

-continued

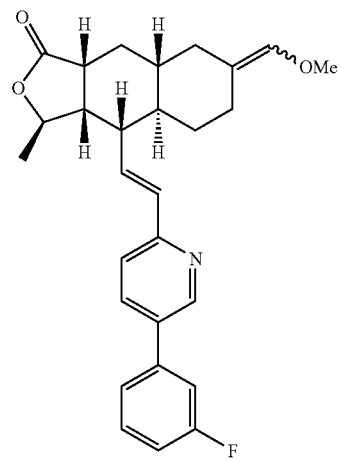

To a suspension of (methoxymethyl)triphenylphosphonium chloride (3.20 g, 9.34 mmol) in 30 ml THF at 0° C. was added 1M $^t$BuOK in THF (10.3 ml, 10.3 mmol) and stirred for 30 min. To this solution was added a solution of ketone (1.95 g, 4.65 mmol) in 25 ml THF and 10 ml DMF. The mixture was stirred at room temperature for 1 hr, poured into 300 ml aq. NH$_4$Cl and extracted with 3×75 ml EtOAc. The combined organic layers were washed with 75 ml brine, dried over MgSO$_4$, filtered, concentrated and chromatographed with 40% EtOAc-hexanes to provide 1.67 g of product.

MS: 448.1 (MH$^+$)

Step 2:

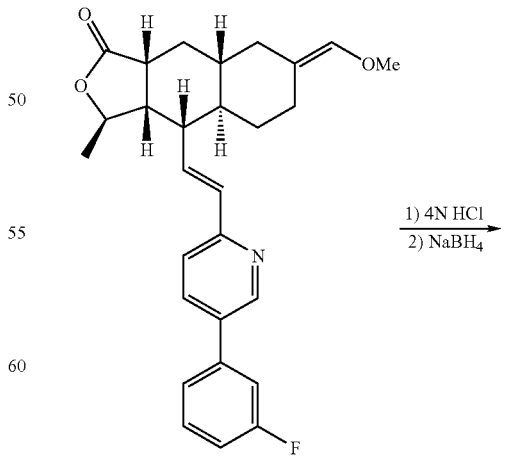

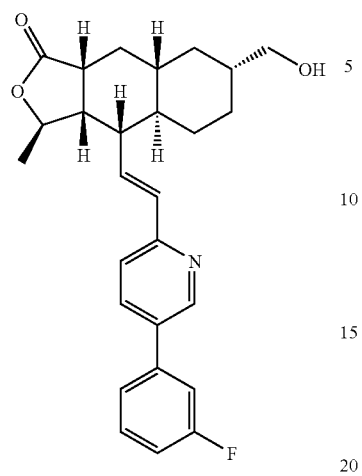

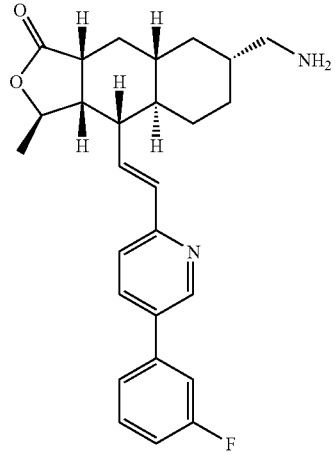

Ex. 74

A solution of 1.67 g of vinyl ether in 15 ml of 4N HCl in dioxane and 1.5 ml H₂O was stirred at room temperature for 1.5 hr, poured into 250 ml of aq. Na₂CO₃ and extracted with 3×50 ml of DCM. The combined organic layers were washed with 50 ml brine, dried over MgSO₄, filtered, concentrated and chromatographed with 40% EtOAc-hexanes to provide 1.36 g of aldehyde.

To a solution of this aldehyde in 20 ml MeOH and 10 ml THF at 0° C. was added 120 mg of NaBH₄ and stirred for 10 min. It was poured into 150 ml of aq. NH₄Cl, and extracted with 3×50 ml EtOAc. The combined organic layer was washed with 50 ml brine, dried over MgSO₄, filtered and concentrated to provide 1.27 g alcohol as white solid.
HRMS: 436.2275 (MH⁺)

To a solution of alcohol (1.27 g, 2.92 mmol) in 20 ml DCM at ca. −40° C. was added 0.63 ml of Et₃N and 0.27 ml of MeSO₂Cl and the solution was allowed to warm up to 0° C. over a period of 1 hr. Then another 0.16 ml of Et₃N and 0.07 ml of MeSO₂Cl was added and stirred for another 1 hr at 0° C. It was diluted with 100 ml EtOAc and washed with 2×30 ml aq. NaHCO₃, 30 ml brine, dried over MgSO₄, filtered and concentrated to provide 1.6 g of mesylate.

A solution of the above mesylate was stirred with 950 mg of NaN₃ (14.6 mmol, 5 equiv.) in 10 ml DMSO at 65° C. for 1.5 hr. It was diluted with 150 ml of EtOAc, washed with 3×50 ml H₂O, 50 ml brine, dried over MgSO₄, filtered and concentrated to provide 1.3 g of azide.

To a solution of this azide in 15 ml EtOAc and 0.2 ml H₂O at 0° C. was added 1M Me₃P in THF and stirred at room temperature for 4 hr. It was concentrated and chromatographed with 4% MeOH-DCM to provide 1.06 g of amine.
HRMS: 435.2445 (MH⁺)

EXAMPLES 75–84

Step 3:

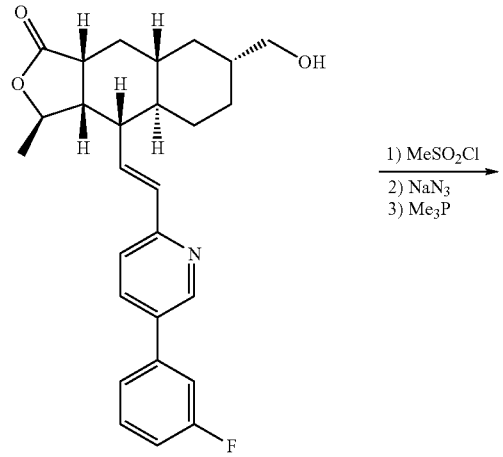

1) MeSO₂Cl
2) NaN₃
3) Me₃P

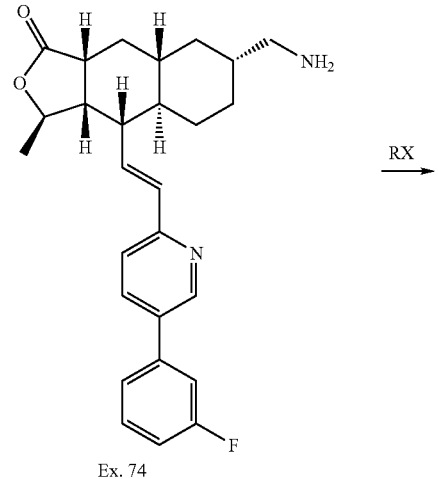

RX

Ex. 74

-continued

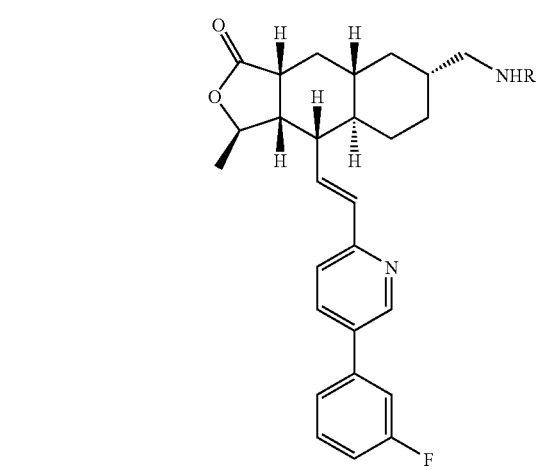

Using the methods described above, the amine was treated with different electrophiles and compounds of the following structure were prepared,

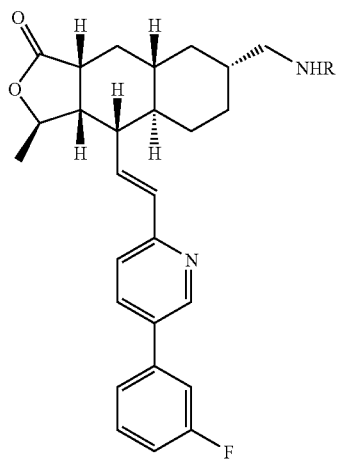

wherein R is as defined in Table 4:

TABLE 4

| Ex. | R | HRMS (MH+) |
|---|---|---|
| 74 | H | 435.2445 |

TABLE 4-continued

| Ex. | R | HRMS (MH+) |
|---|---|---|
| 75 | ethyl ester | 507.2664 |
| 76 | methyl ester | 493.2497 |
| 77 | acetyl | 477.2548 |
| 78 | propanoyl | 491.2703 |
| 79 | methanesulfonyl | 513.2213 |
| 80 | ethanesulfonyl | 527.2388 |
| 81 | alanyl | 506.2822 |
| 82 | prolyl | 532.2970 |
| 83 | ethylcarbamoyl | 506.2822 |
| 84 | piperidine-4-carbonyl | 546.3124 |

EXAMPLES 85–92

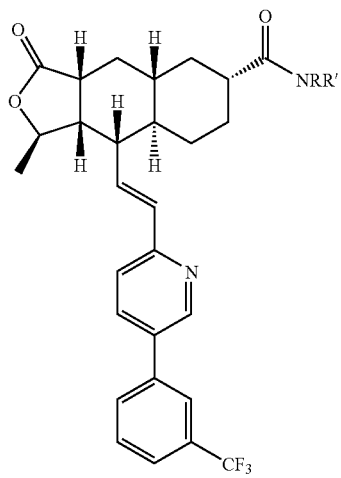

Step 1:

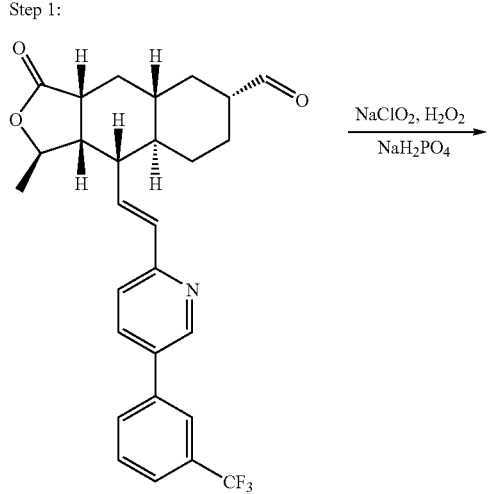

12

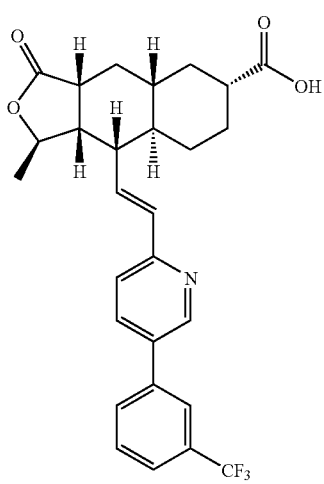

13

To a solution of aldehyde (2.19 g, 4.53 mmol) in 40 ml CH₃CN and 5 ml DCM was added a solution of NaH₂PO₄ (135 mg, 1.13 mmol, 0.25 equiv.) and 30% aq. H₂O₂ (0.51 ml, 4.99 mmol, 1.1 equiv.) in 8 ml H₂O. To this was added a solution of 80% NaClO₂ (0.72 g, 6.37 mmol, 1.4 equiv.) in 5 ml H₂O and the mixture was stirred at room temperature for 2 hr. It was diluted with 150 ml H₂O, acidified with 1N HCl to ca. pH 3 and extracted with 3×50 ml DCM. The combined organic layers were washed with 50 ml brine, dried over MgSO₄, filtered, concentrated to provide 2.2 g of carboxylic acid as solid.

HRMS: 450.2077 (MH$^+$)

Step 2:

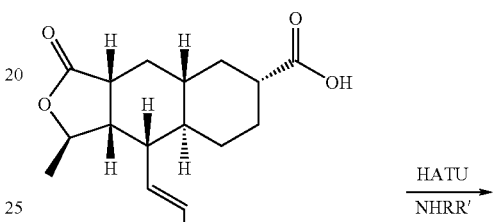

13

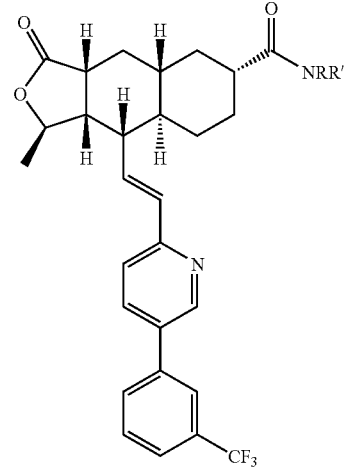

General Procedure:

To a solution of acid and amine (3 equiv.) in DMF-DCM mixture was added HATU (2 equiv.) and stirred overnight at room temperature. It was diluted with EtOAc, washed with aq. NaHCO₃, brine, dried over MgSO₄, filtered, concentrated and chromatographed to provide the amide.

Using the methods described above, compounds of the following structure were prepared:

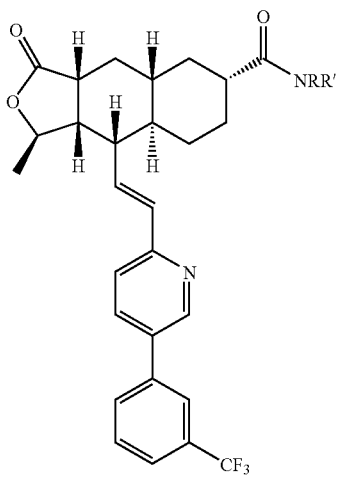

wherein NRR' is as defined in Table 5:

TABLE 5

| EX. | NRR' | (MH+)HRMS |
|---|---|---|
| 85 | -NH-(3-pyridyl) | 576.2481 |
| 86 | -NH-(4-pyridyl) | 576.2472 |
| 87 | -N(H)CH$_3$ | 513.2370 |
| 88 | -N(H)CH$_2$CH$_3$ | 527.2517 |
| 89 | -N(H)CH$_2$CH$_2$OH | 543.2477 |
| 90 | -N(H)CH(CH$_3$)$_2$ | 541.2669 |
| 91 | (S)-3-hydroxypyrrolidinyl | 569.2632 |
| 92 | (R)-3-hydroxypyrrolidinyl | 569.2627 |

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *The Science and Practice of Pharmacy*, 20$^{th}$ Edition, Lippincott Williams & Wilkins, Baltimore, Md., (2000).

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g., nitrogen.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The daily dose of a compound of Formula I for treatment of a disease or condition cited above is about 0.001 to about 100 mg/kg of body weight per day, preferably about 0.001 to about 10 mg/kg. For an average body weight of 70 kg, the dosage level is therefore from about 0.1 to about 700 mg of drug per day, given in a single dose or 2–4 divided doses.

The amount and frequency of administration of the compounds of the invention and/or the pharmaceutically acceptable salts thereof will be regulated according to the judgment of the attending clinician considering such factors as age, condition and size of the patient as well as severity of the symptoms being treated.

Further embodiments of the invention encompass the administration of compounds of Formula I along with at least one additional cardiovascular agent. The contemplated additional cardiovascular agent is one that differs in either atomic make up or arrangement from the compounds of Formula I. Additional cardiovascular agents that can be used in combination with the novel compounds of this invention include drugs which have anti-thrombotic, anti-platelet aggregation, antiatherosclerotic, antirestenotic and/or anti-coagulant activity. Such drugs are useful in treating thrombosis-related diseases including thrombosis, atherosclerosis, restenosis, hypertension, angina pectoris, arrhythmia, heart failure, myocardial infarction, glomerulonephritis, thrombotic and thromboembolic stroke, peripheral vascular diseases, other cardiovascular diseases, cerebral ischemia, inflammatory disorders and cancer, as well as other disorders in which thrombin and its receptor play a pathological role. Suitable cardiovascular agents are selected from the group consisting of thromboxane A2 biosynthesis inhibitors such as aspirin; thromboxane antagonists such as seratrodast, picotamide and ramatroban; adenosine diphosphate (ADP) inhibitors such as clopidogrel; cyclooxygenase inhibitors such as aspirin, meloxicam, rofecoxib and celecoxib; angiotensin antagonists such as valsartan, telmisartan, candesartran, irbesartran, losartan and eprosartan; endothelin antagonists such as tezosentan; phosphodiesterase inhibitors such as milrinoone and enoximone; angiotensin converting enzyme (ACE) inhibitors such as captopril, enalapril, enaliprilat, spirapril, quinapril, perindopril, ramipril, fosinopril, trandolapril, lisinopril, moexipril and benazapril; neutral endopeptidase inhibitors such as candoxatril and ecadotril; anticoagulants such as ximelagatran, fondaparin and enoxaparin; diuretics such as chlorothiazide, hydrochlorothiazide, ethacrynic acid, furosemide and amiloride; platelet aggregation inhibitors such as abciximab and eptifibatide; and GP IIb/IIIa antagonists.

Preferred types of drugs for use in combination with the novel compounds of this invention are thromboxane A2 biosynthesis inhibitors, cyclooxygenase inhibitors and ADP antagonists. Especially preferred for use in the combinations are aspirin and clopidogrel bisulfate.

When the invention comprises a combination of a compound of Formula I and another cardiovascular agent, the two active components may be co-administered simultaneously or sequentially, or a single pharmaceutical composition comprising a compound of Formula I and another cardiovascular agent in a pharmaceutically acceptable carrier can be administered. The components of the combination can be administered individually or together in any conventional dosage form such as capsule, tablet, powder, cachet, suspension, solution, suppository, nasal spray, etc. The dosage of the cardiovascular agent can be determined from published material, and may range from 1 to 1000 mg per dose.

In this specification, the term "at least one compound of Formula I" means that one to three different compounds of Formula I may be used in a pharmaceutical composition or method of treatment. Preferably one compound of Formula I is used. Similarly, the term "one or more additional cardiovascular agents" means that one to three additional drugs may be administered in combination with a compound of Formula I; preferably, one additional compound is administered in combination with a compound of Formula I. The additional cardiovascular agents can be administered sequentially or simultaneously with reference to the compound of Formula I.

When separate compounds of Formula I and the other cardiovascular agents are to be administered as separate compositions, they can be provided in a kit comprising in a single package, one container comprising a compound of Formula I in a pharmaceutically acceptable carrier, and a separate container comprising another cardiovascular agent in a pharmaceutically acceptable carrier, with the compound of Formula I and the other cardiovascular agent being present in amounts such that the combination is therapeutically effective. A kit is advantageous for administering a combination when, for example, the components must be administered at different time intervals or when they are in different dosage forms.

The activity of the compounds of Formula I can be determined by the following procedures.

In Vitro Testing Procedure for Thrombin Receptor Antagonists:

Preparation of [$^3$H]haTRAP

A(pF-F)R(ChA)(hR)(I$_2$—Y)—NH$_2$ (1.03 mg) and 10% Pd/C (5.07 mg) were suspended in DMF (250 μl) and diisopropylethylamine (10 μl). The vessel was attached to the tritium line, frozen in liquid nitrogen and evacuated. Tritium gas (342 mCi) was then added to the flask, which was stirred at room temperature for 2 hours. At the completion of the reaction, the excess tritium was removed and the reacted peptide solution was diluted with DMF (0.5 ml) and filtered to remove the catalyst. The collected DMF solution of the crude peptide was diluted with water and freeze dried to remove the labile tritium. The solid peptide was redissolved in water and the freeze drying process repeated. The tritiated peptide ([$^3$H]haTRAP) was dissolved in 0.5 ml of 0.1% aqueous TFA and purified by HPLC using the following conditions: column, Vydac C18, 25 cm×9.4 mm I.D.; mobile phase, (A) 0.1% TFA in water, (B) 0.1% TFA in CH$_3$CN; gradient, (A/B) from 100/0 to 40/60 over 30 min; flow rate, 5 ml/min; detection, UV at 215 nm. The radiochemical purity of [$^3$H]haTRAP was 99% as analyzed by HPLC. A batch of 14.9 mCi at a specific activity of 18.4 Ci/mmol was obtained.

Preparation of Platelet Membranes

Platelet membranes were prepared using a modification of the method of Natarajan et al (Natarajan et al., *Int. J. Peptide Protein Res.*, vol. 45, pp. 145–151 (1995) from 20 units of platelet concentrates obtained from the North Jersey Blood Center (East Orange, N.J.) within 48 hours of collection. All steps were carried out at 4° C. under approved biohazard safety conditions. Platelets were centrifuged at 100×g for 20 minutes at 4° C. to remove red cells. The supernatants were decanted and centrifuged at 3000×g for 15 minutes to pellet platelets. Platelets were resuspended in 10 mM Tris-HCl, pH 7.5, 150 mM NaCl, 5 mM EDTA, to a total volume of 200 ml and centrifuged at 4400×g for 10 minutes. This step was repeated two additional times. Platelets were resuspended in 5 mM Tris-HCl, pH 7.5, 5 mM EDTA to a final volume of approximately 30 ml and were homogenized with 20 strokes in a Dounce homogenizer. Membranes were pelleted at 41,000×g, resuspended in 40–50 ml 20 mM Tris-HCl, pH 7.5, 1 mM EDTA, 0.1 mM dithiothreitol, and 10 ml aliquots were frozen in liquid N$_2$ and stored at −80° C. To complete membrane preparation, aliquots were thawed, pooled, and homogenized with 5 strokes of a Dounce homogenizer. Membranes were pelleted and washed 3 times in 10 mM triethanolamine-HCl, pH 7.4, 5 mM EDTA, and resuspended in 20–25 ml 50 mM Tris-HCl, pH 7.5, 10 mM MgCl$_2$, 1 mM EGTA, and 1% DMSO. Aliquots of membranes were frozen in liquid N$_2$ and stored at −80° C. Membranes were stable for at least 3 months. 20 units of platelet concentrates typically yielded 250 mg of membrane protein. Protein concentration was determined by a Lowry assay (Lowry et al., *J. Biol. Chem.*, vol. 193, pp. 265–275 (1951).

High Throughput Thrombin Receptor Radioligand Binding Assay

Thrombin receptor antagonists were screened using a modification of the thrombin receptor radioligand binding assay of Ahn et al. (Ahn et al, *Mol. Pharmacol.*, vol. 51, p. 350–356 (1997). The assay was performed in 96 well Nunc plates (Cat. No. 269620) at a final assay volume of 200 μl. Platelet membranes and [$^3$H]haTRAP were diluted to 0.4 mg/ml and 22.2 nM, respectively, in binding buffer (50 mM Tris-HCl, pH 7.5, 10 mM MgCl$_2$, 1 mM EGTA, 0.1% BSA). Stock solutions (10 mM in 100% DMSO) of test compounds were further diluted in 100% DMSO. Unless otherwise indicated, 10 µl of diluted compound solutions and 90 µl of radioligand (a final concentration of 10 nM in 5% DMSO) were added to each well, and the reaction was started by the addition of 100 µl of membranes (40 µg protein/well). The binding was not significantly inhibited by 5% DMSO. Compounds were tested at three concentrations (0.1, 1 and 10 µM). The plates were covered and vortex-mixed gently on a Lab-Line Titer Plate Shaker for 1 hour at room temperature. Packard UniFilter GF/C filter plates were soaked for at least 1 hour in 0.1% polyethyleneimine. The incubated membranes were harvested using a Packard FilterMate Universal Harvester and were rapidly washed four times with 300 µl ice cold 50 mM Tris-HCl, pH 7.5, 10 mM $MgCl_2$, 1 mM EGTA. MicroScint 20 scintillation cocktail (25 µl) was added to each well, and the plates were counted in a Packard TopCount Microplate Scintillation Counter. The specific binding was defined as the total binding minus the nonspecific binding observed in the presence of excess (50 µM) unlabeled haTRAP. The % Inhibition by a compound of [$^3$H]haTRAP binding to thrombin receptors was calculated from the following relationship:

% Inhibition=Total binding−Binding in the presence of a test compound×100 Total binding−Nonspecific binding Affinity values ($K_i$) were then determined using the following formula:

$$K_i = \frac{IC_{50}}{1 + \left[\frac{\text{concentration of radioligand}}{\text{affinity } (K_D) \text{ of radioligand}}\right]}$$

Hence, a lower value of $K_i$ indicates greater binding affinity.

Materials

A(pF-F)R(ChA)(hR)Y—$NH_2$ and A(pF-F)R(ChA)(hR) ($I_2$—Y)—$NH_2$, were custom synthesized by AnaSpec Inc. (San Jose, Calif.). The purity of these peptides was >95%. Tritium gas (97%) was purchased from EG&G Mound, Miamisburg Ohio. The gas was subsequently loaded and stored on an IN/US Systems Inc. Trisorber. MicroScint 20 scintillation cocktail was obtained from Packard Instrument Co.

Protocol for Ex-Vivo Platelet Aggregation in Cynomolgus Whole Blood Drug Administration and Blood Collection:

Conscious chaired cynomolgus monkeys are allowed to equilibrate for 30 min. A needle catheter is inserted into a brachial vein for infusion of test drugs. Another needle catheter is inserted into the other brachial or saphenous vein and used for blood sampling. In those experiments where the compound is administered orally only one catheter is used. A baseline blood sample (1–2 ml) is collected in vacutainer tubes containing a thrombin inhibitor CVS 2139 (100 µg/0.1 ml saline) as an anticoagulant. The drug is then infused intravenously over a period of 30 min. Blood samples (1 ml) are collected at 5, 10, 20, 30 min during and 30, 60, 90 min after termination of the drug infusion. In PO experiments the animals are dosed with the drug using a gavage cannula. Blood samples are collected at 0, 30, 60, 90, 120, 180, 240, 300, 360 min after dosing. 0.5 ml of the blood is used for whole blood aggregation and the other 0.5 ml is used for determining the plasma concentration of the drug or its metabolites. Aggregation is performed immediately after collection of the blood sample as described below.

Whole Blood Aggregation:

A 0.5 ml blood sample is added to 0.5 ml of saline and warmed to 37° C. in a Chronolog whole blood aggregometer. Simultaneously, the impedance electrode is warmed in saline to 37° C. The blood sample with a stir bar is placed in the heating block well, the impedance electrode is placed in the blood sample and the collection software is started. The software is allowed to run until the baseline is stabilized and then a 20 Ω calibration check is performed. 20 Ω is equal to 4 blocks on the graphic produced by the computer software. The agonist (haTRAP) is added by an adjustable volume pipette (5–25 µl) and the aggregation curve is recorded for 10 minutes. Maximum aggregation in 6 minutes following agonist addition is the value recorded.

In vitro Platelet Aggregation Procedure:

Platelet aggregation studies were performed according to the method of Bednar et al. (Bednar, B., Condra, C., Gould, R. J., and Connolly, T. M., *Throm. Res.*, vol. 77, pp. 453–463 (1995)). Blood was obtained from healthy human subjects who were aspirin free for at least 7 days by venipuncture using ACD as anticoagulant. Platelet rich plasma was prepared by centrifugation at 100×g for 15 minutes at 15 deg C. Platelets were pelleted at 3000×g and washed twice in buffered saline containing 1 mM EGTA and 20 µg/ml apyrase to inhibit aggregation. Aggregation was performed at room temperature in buffered saline supplemented with 0.2 mg/ml human fibrinogen. Test compound and platelets were preincubated in 96-well flat-bottom plates for 60 minutes. Aggregation was initiated by adding 0.3 µM haTRAP or 0.1 U/ml thrombin and rapidly vortexing the mixture using a Lab Line Titer Plate Shaker (speed 7). Percent aggregation was monitored as increasing light transmittance at 405 nm in a Spectromax Plate Reader.

In vivo Antitumor Procedure:

Tests in the human breast carcinoma model in nude mouse are conducted according to the procedure reported in S. Even-Ram et. al., *Nature Medicine*, 4, 8, pp. 909–914 (1988).

Compounds of the present invention are surprisingly active in the ex-vivo platelet aggregation test model. In these studies, the compound of Example 2 of this invention, after oral administration at a dose of 0.1 mg/kg, completely inhibited aggregation of platelets induced by exogenously added thrombin receptor activating peptide for duration of 24 hours. Even after 48 hours, approximately 65% of inhibition of platelet aggregation was sustained. In contrast, N-alkyl carbamate analogs, Examples 1A and 2A of U.S. Pat. No 6,063,847, were studied under similar conditions using a dose of 0.5 mg/kg, a 5-fold increase over the dose of the compound of Example 2. Under these conditions, the N-alkyl compounds showed no significant inhibition of platelet aggregation at various time points.

While the present invention has been described in conjunction with the specific embodiments set forth above, many alternatives, modifications and variations thereof will be apparent to those of ordinary skill in the art. All such alternatives, modifications, and variations are intended to fall within the spirit and scope of the present invention.

What is claimed is:

1. A compound of the following formula:

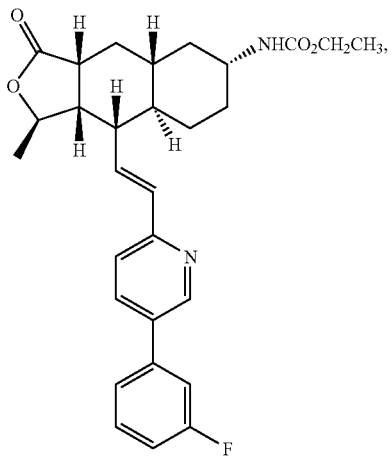

or a pharmaceutically acceptable isomer, salt or solvate thereof.

2. A compound of the following formula:

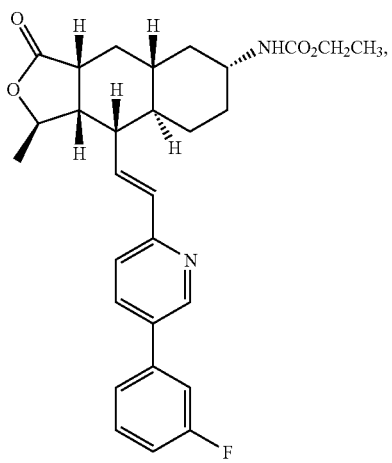

or a pharmaceutically acceptable isomer thereof.

3. A compound of the following formula:

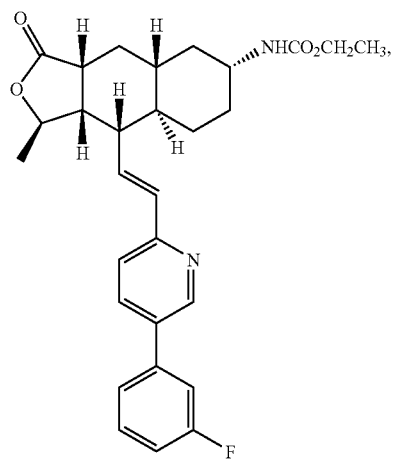

or a pharmaceutically acceptable salt thereof.

4. A bisulfate salt of a compound of the following formula:

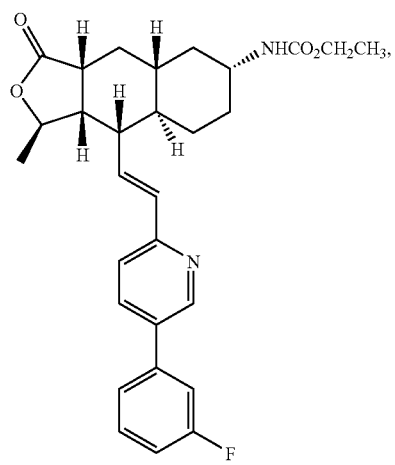

5. A compound of the following formula:

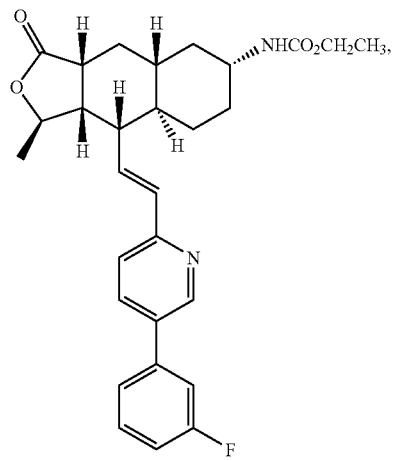

or a pharmaceutically acceptable solvate thereof.

6. A compound of the following formula:

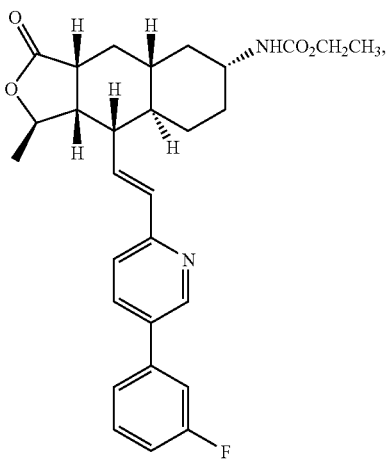

7. A pharmaceutical composition comprising an effective amount of a compound, or a pharmaceutically acceptable isomer, salt or solvate thereof, according to claim 1, and a pharmaceutically acceptable carrier.

8. A pharmaceutical composition comprising an effective amount of a compound or a pharmaceutical acceptable isomer thereof according to claim 2, and a pharmaceutically acceptable carrier.

9. A pharmaceutical composition comprising an effective amount of a compound or a pharmaceutically acceptable salt thereof salt thereof according to claim 3, and a pharmaceutically acceptable carrier.

10. A pharmaceutical composition comprising an effective amount of the bisulfate salt according to claim 4, and a pharmaceutically acceptable carrier.

11. A pharmaceutical composition comprising an effective amount of a compound or a pharmaceutically acceptable solvate thereof according to claim 5, and a pharmaceutically acceptable carrier.

12. A pharmaceutical composition comprising an effective amount of the compound according to claim 6, and a pharmaceutically acceptable carrier.

13. A pharmaceutical composition comprising an effective amount of a compound, or a pharmaceutically acceptable isomer, salt or solvate thereof, according to claim 1, and one or more additional cardiovascular agents selected from the group consisting of aspirin and clopidogrel bisulfate.

14. A pharmaceutical composition comprising an effective amount of a compound or a pharmaceutically acceptable isomer thereof according to claim 2, and one or more additional cardiovascular agents selected from the group consisting of aspirin and clopidogrel bisulfate.

15. A pharmaceutical composition comprising an effective amount of a compound or a pharmaceutically acceptable salt thereof according to claim 3, and one or more additional cardiovascular agents selected from the group consisting of aspirin and clopidogrel bisulfate.

16. A pharmaceutical composition comprising an effective amount of the bisulfate salt according to claim 4, and one or more additional cardiovascular agents selected from the group consisting of aspirin and clopidogrel bisulfate.

17. A pharmaceutical composition comprising an effective amount of a compound or a pharmaceutically acceptable solvate thereof according to claim 5, and one or more additional cardiovascular agents selected from the group consisting of aspirin and clopidogrel bisulfate.

18. A pharmaceutical composition comprising an effective amount of the compound according to claim 6, and one or more additional cardiovascular agents selected from the group consisting of aspirin and clopidogrel bisulfate.

19. A method of treating thrombosis, atherosclerosis, restenosis, hypertension, angina pectoris, arrhythmia, heart failure, myocardial infarction, glomerulonephritis, thrombotic stroke, thromboembolic stroke, peripheral vascular diseases, or cerebral ischemia comprising administering to a mammal an effective amount of a compound, or a pharmaceutically acceptable isomer, salt or solvate thereof, according to claim 1.

20. A method of treating thrombosis, atherosclerosis, restenosis, hypertension, angina pectoris, arrhythmia, heart failure, myocardial infarction, glomerulonephritis, thrombotic stroke, thromboembolic stroke, peripheral vascular diseases, or cerebral ischemia comprising administering to a mammal an effective amount of a compound or a pharmaceutically acceptable isomer thereof according to claim 2.

21. A method of treating thrombosis, atherosclerosis, restenosis, hypertension, angina pectoris, arrhythmia, heart failure, myocardial infarction, glomerulonephritis, thrombotic stroke, thromboembolic stroke, peripheral vascular diseases, or cerebral ischemia comprising administering to a mammal an effective amount of a compound or a pharmaceutically acceptable salt thereof according to claim 3.

22. A method of treating thrombosis, atherosclerosis, restenosis, hypertension, angina pectoris, arrhythmia, heart failure, myocardial infarction, glomerulonephritis, thrombotic stroke, thromboembolic stroke, peripheral vascular diseases, or cerebral ischemia comprising administering to a mammal an effective amount of the bisulfate salt according to claim 4.

23. A method of treating thrombosis, atherosclerosis, restenosis, hypertension, angina pectoris, arrhythmia, heart failure, myocardial infarction, glomerulonephritis, thrombotic stroke, thromboembolic stroke, peripheral vascular diseases, or cerebral ischemia comprising administering to a mammal an effective amount of a compound or a pharmaceutically acceptable solvate thereof according to claim 5.

24. A method of treating thrombosis, atherosclerosis, restenosis, hypertension, angina pectoris, arrhythmia, heart failure, myocardial infarction, glomerulonephritis, thrombotic stroke, thromboembolic stroke, peripheral vascular diseases, or cerebral ischemia comprising administering to a mammal an effective amount of the compound according to claim 6.

25. A method of treating thrombosis, atherosclerosis, restenosis, hypertension, angina pectoris, arrhythmia, heart failure, myocardial infarction, glomerulonephritis, thrombotic stroke, thromboembolytic stroke, peripheral vascular diseases, or cerebral ischemia comprising administering to a mammal an effective amount of a pharmaceutical composition of any of claims 7-18.

26. A method of treating thrombosis comprising administering to a mammal an effective amount of a compound, or a pharmaceutically acceptable isomer, salt or solvate thereof, according to claim 1.

27. A method of treating atherosclerosis comprising administering to a mammal an effective amount of a compound, or a pharmaceutically acceptable isomer, salt or solvate thereof, according to claim 1.

28. A method of treating myocardial infarction comprising administering to a mammal an effective amount of a 28. (continued) compound, or a pharmaceutically acceptable isomer, salt or solvate thereof, according to claim 1.

29. A method of treating thrombotic stroke comprising administering to a mammal an effective amount of a compound, or a pharmaceutically acceptable isomer, salt or solvate thereof, according to claim 1.

30. A method of treating a peripheral vascular disease comprising administering to a mammal an effective amount of a compound, or a pharmaceutically acceptable isomer, salt or solvate thereof, according to claim 1.

31. A method of treating thrombosis comprising administering to a mammal an effective amount of a compound or a pharmaceutically acceptable isomer thereof according to claim 2.

32. A method of treating atherosclerosis comprising administering to a mammal an effective amount of a compound or a pharmaceutically acceptable isomer thereof according to claim 2.

33. A method of treating myocardial infarction comprising administering to a mammal an effective amount of a compound or a pharmaceutically acceptable isomer thereof according to claim 2.

34. A method of treating thrombotic stroke comprising administering to a mammal an effective amount of a compound or a pharmaceutically acceptable isomer thereof according to claim 2.

35. A method of treating a peripheral vascular disease comprising administering to a mammal an effective amount of a compound or a pharmaceutically acceptable isomer thereof according to claim 2.

36. A method of treating thrombosis comprising administering to a mammal an effective amount of a compound or a pharmaceutically acceptable salt thereof according to claim 3.

37. A method of treating atherosclerosis comprising administering to a mammal an effective amount of a compound or a pharmaceutically acceptable salt thereof according to claim 3.

38. A method of treating myocardial infarction comprising administering to a mammal an effective amount of a compound or a pharmaceutically acceptable salt thereof according to claim 3.

39. A method of treating thrombotic stroke comprising administering to a mammal an effective amount of a compound or a pharmaceutically acceptable salt thereof according to claim 3.

40. A method of treating a peripheral vascular disease comprising administering to a mammal an effective amount of a compound or a pharmaceutically acceptable salt thereof according to claim 3.

41. A method of treating thrombosis comprising administering to a mammal an effective amount of a bisulfate salt according to claim 4.

42. A method of treating atherosclerosis comprising administering to a mammal an effective amount of a bisulfate salt according to claim 4.

43. A method of treating myocardial infarction comprising administering to a mammal an effective amount of a bisulfate salt according to claim 4.

44. A method of treating thrombotic stroke comprising administering to a mammal an effective amount of a bisulfate salt according to claim 4.

45. A method of treating a peripheral vascular disease comprising administering to a mammal an effective amount of a bisulfate salt according to claim 4.

46. A method of treating thrombosis comprising administering to a mammal an effective amount of a compound or a pharmaceutically acceptable solvate thereof according to claim 5.

47. A method of treating atherosclerosis comprising administering to a mammal an effective amount of a compound or a pharmaceutically acceptable solvate thereof according to claim 5.

48. A method of treating myocardial infarction comprising administering to a mammal an effective amount of a compound or a pharmaceutically acceptable solvate thereof according to claim 5.

49. A method of treating thrombotic stroke comprising administering to a mammal an effective amount of a compound or a pharmaceutically acceptable solvate thereof according to claim 5.

50. A method of treating a peripheral vascular disease comprising administering to a mammal an effective amount of a compound or a pharmaceutically acceptable solvate thereof according to claim 5.

51. A method of treating thrombosis comprising administering to a mammal an effective amount of a compound according to claim 6.

52. A method of treating atherosclerosis comprising administering to a mammal an effective amount of a compound according to claim 6.

53. A method of treating myocardial infarction comprising administering to a mammal an effective amount of a compound according to claim 6.

54. A method of treating thrombotic stroke comprising administering to a mammal an effective amount of a compound according to claim 6.

55. A method of treating a peripheral vascular disease comprising administering to a mammal an effective amount of a compound according to claim 6.

56. A method of treating thrombosis comprising administering to a mammal an effective amount of a pharmaceutical composition of any of claims 7-18.

57. A method of treating atherosclerosis comprising administering to a mammal an effective amount of a pharmaceutical composition of any of claims 7-18.

58. A method of treating myocardial infarction comprising administering to a mammal an effective amount of a pharmaceutical composition of any of claims 7-18.

59. A method of treating thrombotic stroke comprising administering to a mammal an effective amount of a pharmaceutical composition of any of claims 7-18.

60. A method of treating a peripheral vascular disease comprising administering to a mammal an effective amount of a pharmaceutical composition of any of claims 7-18.

61. A method of inhibiting platelet aggregation comprising administering to a mammal an effective amount of a compound, or a pharmaceutically acceptable isomer, salt or solvate thereof, according to claim 1.

62. A method of inhibiting platelet aggregation comprising administering to a mammal an effective amount of a compound or a pharmaceutically acceptable isomer thereof according to claim 2.

63. A method of inhibiting platelet aggregation comprising administering to a mammal an effective amount of a compound or a pharmaceutically acceptable salt thereof according to claim 3.

64. A method of inhibiting platelet aggregation comprising administering to a mammal an effective amount of a bisulfate salt according to claim 4.

65. A method of inhibiting platelet aggregation comprising administering to a mammal an effective amount of a compound or a pharmaceutically acceptable solvate thereof according to claim 5.

66. A method of inhibiting platelet aggregation comprising administering to a mammal an effective amount of a compound according to claim 6.

67. A method of inhibiting platelet aggregation comprising administering to a mammal an effective amount of a pharmaceutical composition of any of claims 7-18.

* * * * *

UNITED STATES PATENT AND TRADEMARK OFFICE
CERTIFICATE OF CORRECTION

PATENT NO. : 7,304,078 B2  Page 1 of 1
APPLICATION NO. : 10/412982
DATED : December 4, 2007
INVENTOR(S) : Samuel Chackalamannil et al.

It is certified that error appears in the above-identified patent and that said Letters Patent is hereby corrected as shown below:

In the Claims:

Claim 8, col. 57, line 28, please correct "pharmaceutical" to:

-- pharmaceutically --

Signed and Sealed this

Twenty-fourth Day of November, 2009

David J. Kappos
*Director of the United States Patent and Trademark Office*

UNITED STATES PATENT AND TRADEMARK OFFICE

(12)      CERTIFICATE EXTENDING PATENT TERM
UNDER 35 U.S.C. § 156

| | | | |
|---|---|---|---|
| (68) | PATENT NO. | : | 7,304,078 |
| (45) | ISSUED | : | December 4, 2007 |
| (75) | INVENTOR | : | Samuel Chackalamannil et al. |
| (73) | PATENT OWNER | : | Aralez Pharmaceuticals Trading DAC |
| (95) | PRODUCT | : | ZONTIVITY® (vorapaxar sulfate) |

This is to certify that an application under 35 U.S.C. § 156 has been filed in the United States Patent and Trademark Office, requesting extension of the term of U.S. Patent No. 7,304,078 based upon the regulatory review of the product ZONTIVITY® (vorapaxar sulfate) by the Food and Drug Administration. According to United States Patent and Trademark Office records, the original expiration date of the patent as of the date of issuance of this certificate is April 6, 2024. Because it appears that the requirements of the law have been met, this certificate extends the term of the patent for the period of

(94)                          1,356 days subject to the payment of maintenance fees as provided by law, with all rights pertaining thereto as provided by 35 U.S.C. § 156.

I have caused the seal of the United States Patent and Trademark Office to be affixed this 3rd day of September 2020.

Andrei Iancu
Under Secretary of Commerce for Intellectual Property and
   Director of the United States Patent and Trademark Office